United States Patent
Werthman et al.

(10) Patent No.: US 8,169,191 B2
(45) Date of Patent: May 1, 2012

(54) SYSTEM FOR USE IN GATHERING OR PROCESSING DATA IN A HEALTHCARE FACILITY HAVING FLEET OF MOBILE WORKSTATIONS

(76) Inventors: Dean A. Werthman, Murfreesboro, TN (US); Gary Coonan, Rockvale, TN (US); Ary Inthaluxay, Murfreesboro, TN (US)

( * ) Notice: Subject to any disclaimer, the term of this patent is extended or adjusted under 35 U.S.C. 154(b) by 1070 days.

(21) Appl. No.: 12/072,281

(22) Filed: Feb. 25, 2008

(65) Prior Publication Data

US 2009/0212744 A1 Aug. 27, 2009

(51) Int. Cl.
 *H02J 7/00* (2006.01)
(52) U.S. Cl. .......... 320/132; 320/107; 320/116
(58) Field of Classification Search ........... 320/107, 320/112–116, 132
See application file for complete search history.

(56) References Cited

U.S. PATENT DOCUMENTS

| | | | |
|---|---|---|---|
| 4,395,696 A | 7/1983 | Menard | |
| 4,739,242 A | 4/1988 | McCarty et al. | |
| 5,703,751 A | 12/1997 | Huang | |
| 5,784,626 A | 7/1998 | Odaohara | |
| 5,806,943 A | 9/1998 | Dell et al. | |
| 5,842,030 A | 11/1998 | Larabell et al. | |
| 5,914,585 A | 6/1999 | Grabon | |
| 6,137,260 A | 10/2000 | Wung et al. | |
| 6,160,376 A | 12/2000 | Kumar et al. | |
| 6,169,387 B1 * | 1/2001 | Kaib | 320/132 |
| 6,183,417 B1 | 2/2001 | Geheb et al. | |
| 6,493,217 B1 | 12/2002 | Jenkins, Jr. | |
| 6,493,220 B1 | 12/2002 | Clark et al. | |
| 6,539,484 B1 | 3/2003 | Cruz | |
| 6,741,065 B1 | 5/2004 | Ishii et al. | |
| 7,130,190 B1 | 10/2006 | Baker | |
| 7,148,580 B2 | 12/2006 | Sodemann et al. | |
| 2001/0020838 A1 | 9/2001 | Malackowski | |
| 2002/0005196 A1 | 1/2002 | Brugger | |
| 2006/0030973 A1 | 2/2006 | Brillon | |
| 2007/0024246 A1 | 2/2007 | Flaugher | |
| 2007/0216355 A1 | 9/2007 | Kim | |

OTHER PUBLICATIONS

ISA, PCT International Search Report, May 5, 2009, 2 pages.
ISA, Written Opinion of International Searching Authority, May 5, 2009, 5 pages.
WIPO, PCT International Report on Patentability, Aug. 31, 2010, pp. 1-8.

* cited by examiner

*Primary Examiner* — Samuel Berhanu
(74) *Attorney, Agent, or Firm* — Liell & McNeil

(57) ABSTRACT

A system for use in gathering and/or processing data in healthcare facilities includes a fleet of mobile workstations, a set of interchangeable batteries for the fleet of mobile workstations and a battery recharging system for the set of interchangeable batteries. The battery recharging system includes a common battery charger and a control device configured to reduce variation in charging cycle count among the batteries at least in part by outputting a battery selection signal in response to comparing charging cycle counts for each of the batteries.

19 Claims, 11 Drawing Sheets

SYSTEM FOR USE IN GATHERING OR PROCESSING DATA IN A HEALTHCARE FACILITY HAVING FLEET OF MOBILE WORKSTATIONS

TECHNICAL FIELD

The present disclosure relates generally to a system for use in gathering or processing data in a healthcare facility, and relates more particularly to reducing variation in charging cycle count among a plurality of interchangeable batteries for use in such a system.

BACKGROUND

Mobile workstations are well known and widely used in a variety of environments. A typical mobile workstation includes a frame mounted on a wheeled base, and a work platform or the like mounted above the wheeled base. A computer display may be mounted on or in proximity to the work platform such that the mobile workstation can be transported about and computer-based activities performed at different locations. Hospitals, clinics and other institutions commonly use one or more fleets of mobile workstations for administering patient care. For example, each floor of a hospital may have a fleet comprising a plurality of mobile workstations which are each available for use by one or more staff members. Certain of the mobile workstations of a given fleet may be substantially identical for general use, while others may be purpose-built or configured for more specific tasks. In a typical hospital or clinic environment, mobile workstations may be equipped with data gathering and/or data processing instruments such that facility personnel can move a mobile workstation from room to room, monitoring patient status, performing healthcare diagnostics or other activities such as dispensing medication, refilling supplies, etc. The computers resident on each mobile workstation typically enable a range of activities. Using the resident computer, facility personnel can enter patient-related data, check patient healthcare charts and medication dosage, authorization and scheduling of various treatments, etc. Over the years, a great many technological advances in the art of mobile workstations have improved both patient care quality and healthcare administration efficiency.

In decades past, mobile workstations consisted largely of vehicles for transporting computers from one room in a healthcare facility to another. A user typically moved the mobile workstation to a patient's bedside, then entered relevant patient data, or referenced patient data stored on the computer resident on the mobile workstation while performing various tasks. Information from the mobile workstation could then be later uploaded directly or indirectly from the workstation computer to a central database of the facility. Mobile workstations thus came to be used principally as satellite data gathering units or reference stations, with much of the processing and analysis of data being performed at a central location.

In more recent years, diagnostic and/or monitoring equipment and other peripheral devices have been mounted on and used in connection with mobile workstations, distributing some data processing among the different units. A rise in the demands placed on computers resident on mobile workstations by native hospital or clinic applications, however, has limited the practicality of supporting peripheral devices with resident workstation computers.

One shortcoming of many earlier mobile workstations was the requirement that they be plugged into a wall electrical outlet in a facility. It has become common for many mobile workstations to include a rechargeable battery carried thereon, so that connection to a wall outlet need only take place periodically for recharging. One consequence of using rechargeable batteries, however, has been the downtime and inconvenience required to recharge workstation batteries at a wall outlet. While certain rechargeable batteries can power a workstation for hours, the associated workstation is still idled for the typically lengthy recharging period. Thus, electrical cords are still needed at some point during a typical workstation's service cycle. Extra workstations may also be needed to ensure that a sufficient number are available for use by facility personnel at any given time, as certain workstations can typically be expected to be idled for recharging.

Attempts have been made to overcome certain of the problems associated with rechargeable batteries, namely, the downtime required for recharging. Designs have been proposed where a rechargeable battery may be switched with a fresh battery rather than docking the workstation at a wall outlet. These proposals have seen little, if any commercial success, for several reasons. First, conventional batteries tend to be quite heavy and unwieldy. It is thus difficult and in some instances even dangerous for facility personnel to attempt to remove a conventional, relatively heavy lead-acid battery, for example, and replace it on a mobile workstation with a similarly heavy and unwieldy lead-acid battery. A second problem is that the workstation must still typically be powered down during switching batteries. Many users have considered these factors to render switchable battery systems more trouble than they are worth.

SUMMARY

In one aspect, a system for use in gathering or processing data in a healthcare facility includes a fleet of mobile workstations each including a computerized device having a computer readable data storage medium and a battery input interface. The system further includes a set of interchangeable batteries each configured to couple with the battery input interface of any one of the mobile workstations for providing power to the corresponding computerized device. The system still further includes a batter recharging system for the set of interchangeable batteries including a common battery charger having a plurality of docking stations, each of the docking stations including a battery charging interface, and a control device coupled with each of the battery charging interfaces. The control device is configured to receive inputs indicative of at least one of, battery identification and charging cycle count, via each of the battery charging interfaces. The control device is further configured to output a battery selection signal based at least in part on the inputs.

In another aspect, a method of reducing variation in charging cycle count among a plurality of interchangeable batteries for a fleet of mobile workstations includes the steps of, docking a plurality of interchangeable batteries with a common battery charger, and receiving inputs associated with a charging cycle count for each of the plurality of interchangeable batteries. The method still further includes a step of outputting a battery selection signal which is based at least in part on the inputs.

DETAILED DESCRIPTION

Figure 1:
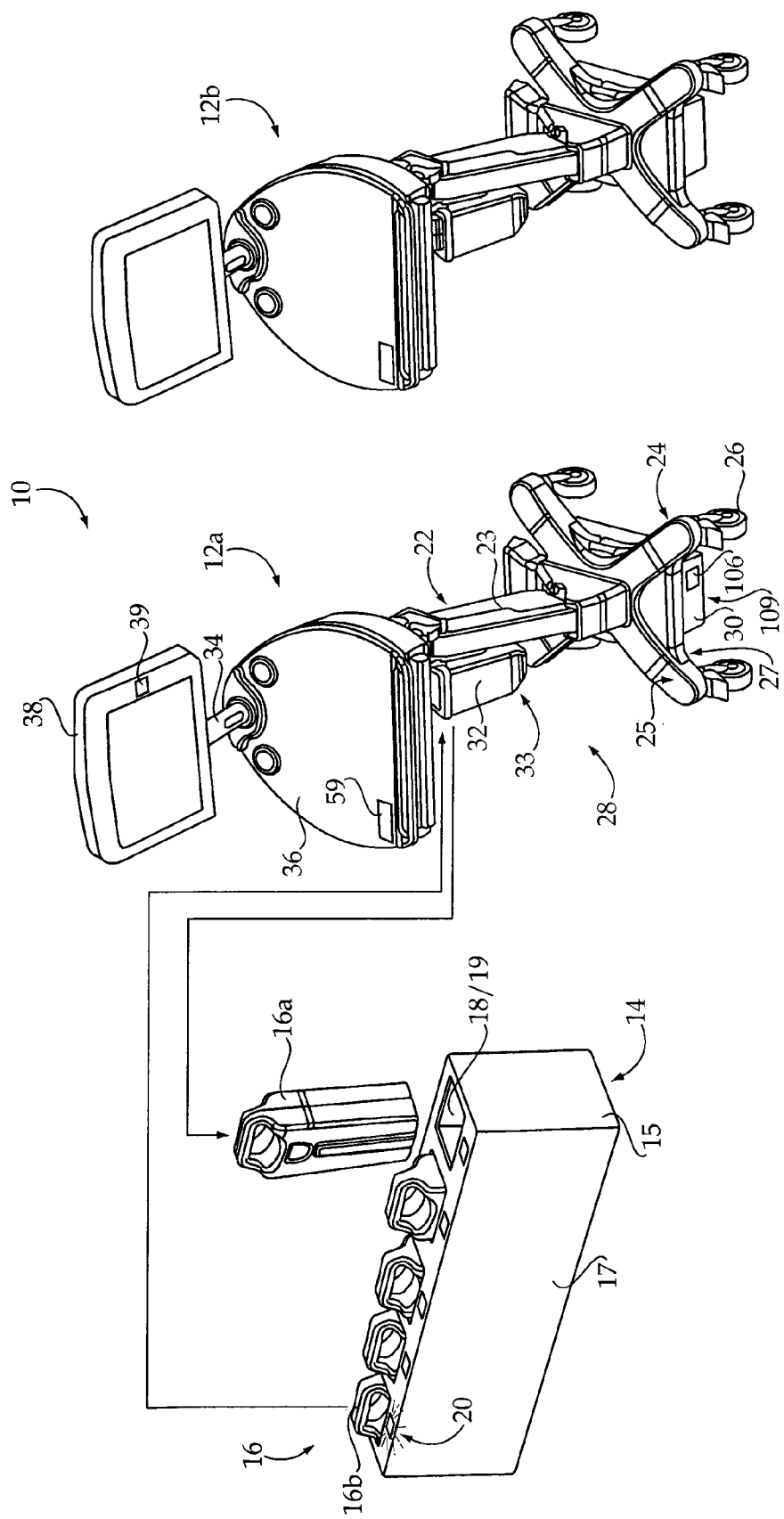
FIG. 1 is a diagrammatic view of a system for gathering or processing data in a healthcare facility, according to one embodiment.

Referring to FIG. 1, there is shown a system 10 for use in gathering or processing data in a healthcare facility, and also amenable to other uses, as further described herein. System 10 may include a fleet of mobile workstations, including a first mobile workstation 12a and a second mobile workstation 12b. System 10 might also include more than two mobile workstations, and embodiments are contemplated wherein many workstations will comprise the fleet of mobile workstations represented by workstations 12a and 12b in FIG. 1. For instance, one floor or wing of a hospital, clinic, etc., might include one mobile workstation for each of a plurality of employees whom are each assigned to a set of patient rooms, totaling a dozen or more mobile workstations for each floor or wing. Workstations 12a and 12b may be substantially identical in one embodiment, and therefore references herein to workstation 12a or 12b should be understood to similarly refer to corresponding features of the other of workstations 12a and 12b. In other embodiments, workstations 12a and 12b might be different from one another. In the embodiment shown, workstation 12a includes a computerized device 38 comprising for example, a flat screen computer monitor, and a computer readable data storage medium 39. Computerized device 38 may be mounted to a frame 22 of workstation 12a via a mount 34. Frame 22 may further include a frame or body component (not numbered) having a work platform 36 that is disposed adjacent computerized device 38. Workstations 12a and 12b may be used in a conventional hospital or clinic setting, wherein personnel can use workstations 12a, 12b to move about the hospital, clinic, etc. to gather patient healthcare data, process patient healthcare data, or for a variety of other purposes.

Frame 22 may further include a wheeled base 24 which has an upper side 25, and a lower side 27 to which a plurality of wheels 26 are mounted to enable mobility of workstation 12a. Frame 22 may further include a support arm assembly 23 which extends vertically upwardly from upper side 25 of base 24 to support computerized device 38, and the portion of frame 22 which includes work platform 36. Workstation 12a may further include a power system 28 which includes a control system 109 having at least a portion of its components housed in a control system housing 30, for controlling, monitoring, etc., a variety of functions and features of workstation 12a, as further described herein. In one embodiment, power system 28 may include a back-up battery 106 mounted in control system housing 30. Power system 28 may further include a battery docking station 32 which comprises a battery input interface 33, and is configured for docking a removable battery therewith for supplying power to workstation 12a. As will be further apparent from the following description, back-up battery 106 may be used in providing electrical power to power system 28, and thenceforth to other systems, subsystems and components of workstation 12a during swapping a removable battery from battery docking station 38 with a substitute removable battery.

In one embodiment, system 10 may include a set 13 of interchangeable batteries 16, each one of which is configured to couple with battery input interface 33 via docking in docking station 32, as well as with any one of the other battery input interfaces associated with other mobile workstations of system 10. In FIG. 1, a first battery assembly 16a which includes a first battery of set 13 and a second battery assembly 16b which includes a second battery of set 13, are shown. When using workstation 12a, 12b of system 10, a battery docked with the corresponding docking station 32 may be swapped with a substitute battery once discharged. Thus, personnel may use workstations 12a, 12b to make rounds, for example, gathering and/or processing data in a healthcare facility or otherwise administering patient care, monitoring or evaluation. Once removable batteries coupled with workstations 12a, 12b are discharged, or are nearly discharged, workstations 12a and 12b may be taken to a given location where substitute batteries are available, and the substitute batteries swapped with the discharged batteries coupled with each workstation 12a, 12b. By using a back-up battery 106 with each workstation 12a, 12b, operation of system 10 may be essentially seamless, and substitute batteries swapped with discharged batteries, without requiring workstations 12a, 12b to power down, as further described herein. This capability is contemplated to provide substantial advantages over earlier strategies where workstations were plugged into a wall outlet for recharging or where workstations had to be powered down to change batteries.

System 10 may further include a battery recharging system 14 for recharging set 13 of interchangeable batteries. Battery recharging system 14 may include a common battery charger 15 which includes a plurality of docking stations 18, each having a battery charging interface 19. Battery charger 15 may further include a housing 17 wherein each of the docking stations 18 are disposed. The use of common battery charger 15 in the manner described herein will enable reducing variation in charging cycle count among the interchangeable batteries of set 13. Since battery set 13 includes a plurality of batteries, each of which may be coupled with one of workstations 12a, 12b at any one time, certain batteries might be used, and thus discharged and recharged, a greater number of times than others, without some means to reduce variability in charging cycle count. The present disclosure addresses this need by way of a unique strategy for reducing charging cycle count, as further described herein, and thus preventing relative overuse or underuse of any of the batteries of set 13.

Figure 2:
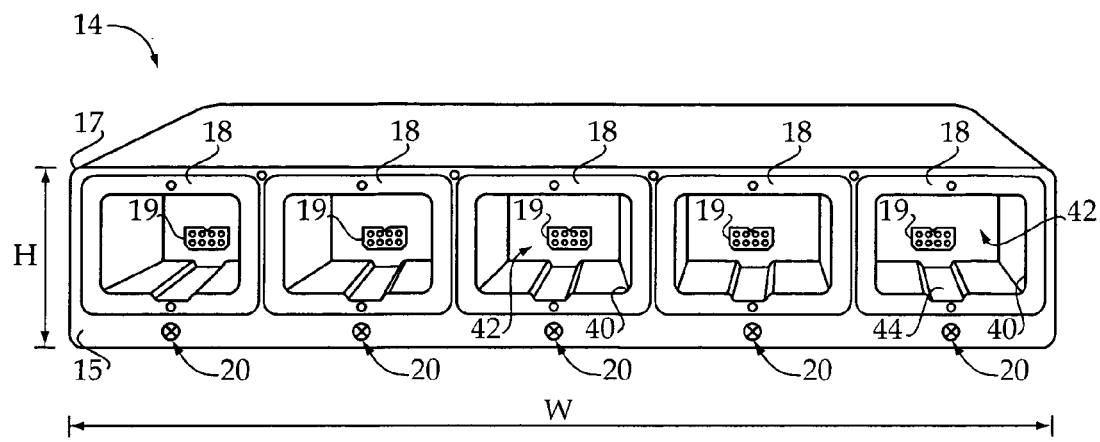
FIG. 2 is a front view of a battery charger according to one embodiment.

Turning now to FIG. 2, there is shown battery charger 15 as viewed towards each of docking stations 18. Each of docking stations 18 may include a first, open end 40 and a second, blind end 42. Each of battery charging interfaces 19 may be disposed at the corresponding second end 42, and may comprise a multi-pin connector such as an eight-pin connector. It may be noted that housing 17 includes a width W, and a height H. Width W may be several times height H, and docking stations 18 may be distributed side by side along width W. In a healthcare facility or other institution, battery charger 15 might be wall mounted with docking stations 18 positioned more or less horizontally at a height such that batteries of set 13 can be readily docked with each docking station 18 by sliding the respective batteries therein. Other battery charger configurations, docking station number and docking station orientations are also contemplated herein, and the present description of battery charger 15 should not be taken as limiting.

Each of docking stations 18 may further include a key 44 which is configured to orient a removable battery in a single desired orientation when docked with the corresponding docking station 18. This can allow appropriate alignment between a pin-type connector of a removable battery and battery charging interfaces 19. In one embodiment, key 44 may comprise an involute flute 44. Each of docking stations 18 may further define a guide for battery docking having a narrowing taper from first end 40 towards second end 42. In one embodiment, a width of each of docking stations 18, corresponding with width W, may narrow in a direction from first end 40 towards second end 42, whereas a height of each docking station 18 may be uniform from first end 40 towards second end 42. In other embodiments, each docking station 18 might have both a uniform width and height, or could include non-uniform widths and heights, for example narrowing widths and narrowing heights. Furthermore, while the use of key 44 is contemplated to be one practical implementation strategy, other embodiments are contemplated in which removable batteries might be docked with docking station 18 in a plurality of different orientations, or where another means of ensuring a single docking orientation is provided.

Battery charger 15 may further include at least one indicating device 20 which has a plurality of different indicating states, and is configured to switch between the plurality of states in response to a battery selection signal, further described herein. In one embodiment, the at least one indicating device may include a plurality of lights 20, each having an illuminated state and an unilluminated state. Accordingly, battery charger 15 may be configured to indicate a selected one of a plurality of batteries simultaneously docked with a plurality of docking stations 18, for selection by a user. As further explained herein, the battery which is indicated for use via battery charger 15 may be a recharged battery having the lowest charging cycle count of a plurality of batteries simultaneously docked with battery charger 15. Thus, when implemented in the context of system 10, personnel may transport one of workstations 12a, 12b to battery recharging system 14, then swap a discharged battery for the fully charged battery in battery charger 15 which has the lowest charging cycle count, as indicated by way of indicating device(s) 20. While five battery docking stations are shown, in other embodiments only two battery docking stations might be used, or a greater number such as ten or more. The number of docking stations selected for use in battery charger 15 may be a function of a number of batteries of system 10, a number of mobile workstations of system 10, an expected time duration between battery charging cycles, expected time duration of a battery charging cycle, and still other factors.

Figure 3:
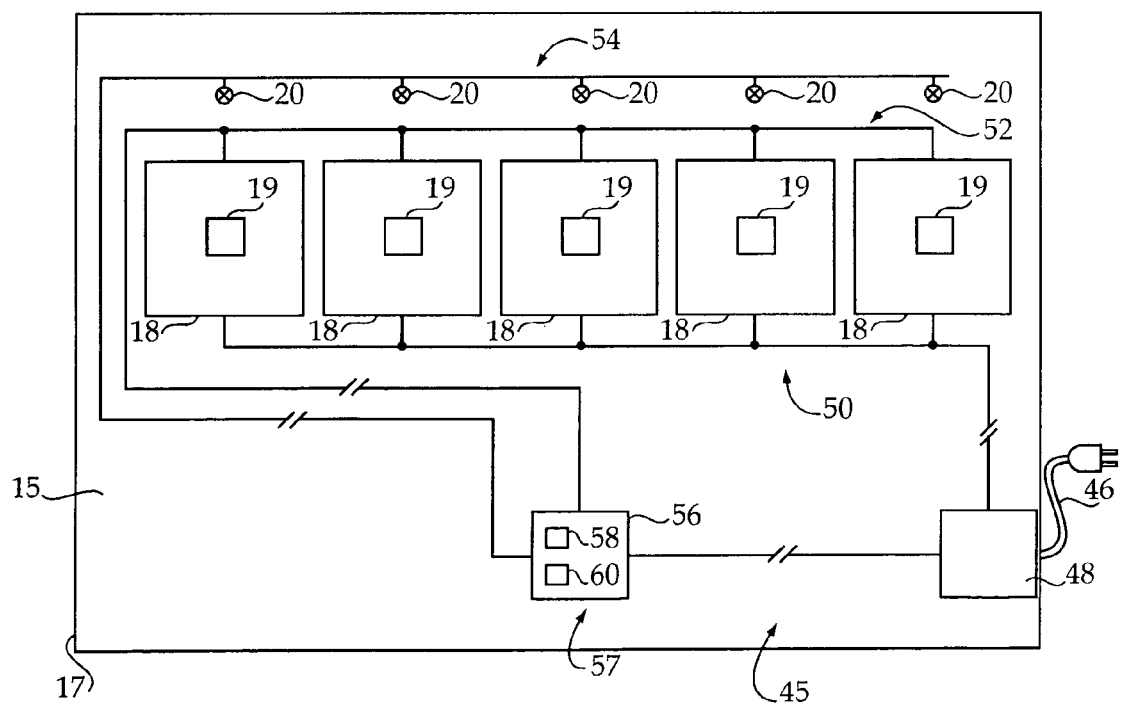
FIG. 3 is a block diagram of the battery charger of FIG. 2.

Turning now to FIG. 3, there is shown a schematic view of battery charger 15 which is illustrative of certain features and functions which enable reducing variability in charging cycle count. Battery charger 15 may include an electrical power system 45 which is connected with an electrical connector 46 configured to connect with a conventional AC electrical power supply (not shown) in a healthcare facility or other institution. Power system 45 may include an input interface 48 such as an AC-DC interface which connects to a power bus 50 configured to supply electrical power to battery charging interfaces 19 associated with each one of battery docking stations 18. Battery charging system 14 may also include at least one battery charging cycle counter 57. In one embodiment, battery charging cycle counter 57 may be resident on battery charger 15, although in other embodiments battery charging cycle counter 57 might be positioned elsewhere in system 14 such as on one or more of batteries of set 13. The at least one battery charging cycle counter 57 may be part of a control device 56 such as an electronic control unit 56 having a microprocessor 58 and a computer readable memory 60. Memory 60, as well as the other computer readable data storage media described herein, may comprise any suitable type of memory. In embodiments where charging cycle counter 57 is resident on battery charger 15, memory 60 may comprise a writable memory. In other embodiments, wherein the primary or sole purpose of memory 60 is to store computer executable instructions for microprocessor 58, memory 60 might comprise a read-only memory. Electronic control unit 56, or another control device, may be coupled with each of battery charging interfaces 19 by way of a first communication bus 52. Electronic control unit 56 may be coupled with the at least one indicating device 20 by way of a second communication bus 54.

In one embodiment, electronic control unit 56 may be configured to receive inputs via each of battery charging interfaces 19 which are indicative of at least one of, battery identification and charging cycle count. Electronic control unit 56 may be further configured to determine a charging cycle count for each one of a plurality of interchangeable batteries simultaneously docked with battery docking stations 18. In one embodiment, electronic control unit 56 might receive battery identification data via each battery charging interface 19 which enables electronic control unit 56 to identify the particular battery coupled with each one of battery charging interfaces 19. In such an embodiment, electronic control unit 56 might utilize charging cycle counts for the identified batteries stored in memory 60 to determine how many times each one of the identified batteries docked with charger 15 has been charged. In another embodiment, electronic control unit 56 may receive charging cycle count data stored on a memory resident on each one of a plurality of batteries docked with battery charger 15 via each battery charging interface 19. In such an embodiment, each of the plurality of batteries might be understood as having the charging cycle counter resident thereon. In either case, electronic control unit 56 can determine the number of times that each of a plurality of batteries docked therewith has been charged, and can output a battery selection signal via communication bus 54 to illuminate a selected one of indicating devices 20 which corresponds with the docking station 18 or battery charging interface 19 with which the selected battery is coupled. In this general manner, personnel operating workstations 12a, 12b of system 10 can be notified as to an appropriate battery to select from battery charger 15. As illustrated in FIG. 1, first battery assembly 16a may be removed from battery docking station 32 of mobile workstations 12a and swapped with second battery assembly 16b, which has been identified in battery charger 15 by illuminating an appropriate light of indicating device 20.

It will be recalled that batteries selected from battery charger 15 for swapping with batteries on one of workstations 12a and 12b will typically be fully charged or nearly fully charged. The reasons for this will be readily apparent. To this end, the process of selecting and indicating an appropriate battery for swapping out of battery charger 15 may not only include counting battery charging cycles, it may also include determining which of a plurality of batteries docked with charger 15 is at or above a predetermined charge status level. To this end, electronic control unit 56 may be configured to assign a subset of a plurality of interchangeable batteries docked with charger 15 to a first category such as an available category, if an indicated charge status for the subset is above a predetermined level. Electronic control unit 56 may further be configured to assign another subset of the plurality of interchangeable batteries to a second category such as an unavailable category, if the indicated charge status for the subset is below a predetermined level. The one or more batteries assigned to the available category may be the ones whose charging cycle count is presently evaluated for selection of an appropriate battery. The predetermined level of charge status for the first subset might be the same as the predetermined level of charge status for the second subset in certain embodiments.

In still other embodiments, additional factors relating to battery use characteristics, charge status, and charging cycle count might be used in selecting an appropriate battery for use. For instance, embodiments are contemplated wherein battery charger 15 comprises a system in which on time duration, off time duration, number of power-up and power-down cycles, temperature and still other factors are considered in selecting an appropriate battery from charger 15. It is thus contemplated that for certain systems a multivariate recipe may exist for optimum battery selection. Electronic control unit 56 could use a look-up table or the like having two or more dimensions to select an appropriate battery for use based a plurality of different factors. It is contemplated, however, that in at least certain embodiments determining a selected battery and outputting a corresponding battery selection signal may be based solely on charging cycle counts among a plurality of recharged batteries simultaneously docked with docking stations 18.

Figure 5:
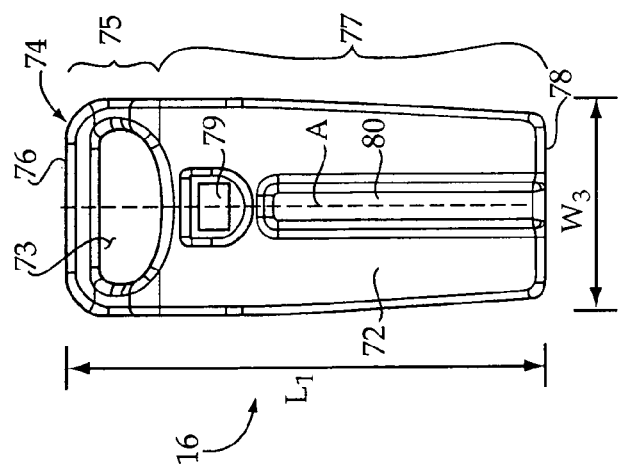
FIG. 5 is a front view in elevation of a power supply unit according to one embodiment.

Turning now to FIG. 5, there is shown an elevational view from one side of a power supply unit 16 suitable for use in system 10, or in a variety of other applications. The present description of power supply unit 16 should be understood to refer to corresponding or identical features of any of the other battery assemblies used in connection with system 10, such as battery assemblies 16a and 16b shown in FIG. 1. Power supply unit 16 may comprise a battery assembly 16 including an elongate housing 72 formed of a molded plastic material having a first segment 75 and a second segment 77. Housing 72 may further include a first end 76, and a second end 78. In one embodiment, first segment 75 may include a handle 74 for manipulating battery assembly 16, and defining a void 73 together with the portion of housing 72 making up second segment 77. Battery assembly 16 may further include a display device 79, such as an LCD display, positioned on housing 72 and configured to display data associated with internal components and/or processes of battery assembly 16, as further described herein. Battery assembly 16 may further include a key 80, for example comprising a longitudinal exvolute flute, which is configured to orient battery assembly 16 for docking with a battery docking station such as one of battery docking stations 18 of charger 15 or battery docking station 32 of mobile workstation 12a. It will be recalled that each of battery docking stations 18 also includes a key 44, and thus mating between keys 80 and 44 can ensure that battery assembly 16 is docked in the corresponding docking station in an appropriate orientation. As further described herein, docking station 32 of workstation 12a may have a configuration similar or identical to that shown and described with regard to docking stations 18 of battery charger 15. Housing 72 may also include a length $L_1$ extending from first end 76 to second end 78. Housing 72 may also include a first width dimension $W_3$ which is oriented perpendicular to its length $L_1$, and also perpendicular to a longitudinal axis A of housing 72. In one embodiment, width $W_3$ may be nonuniform and may become smaller in a direction from first end 76 towards second end 78.

It will be recalled that docking stations 18 each comprise a narrowing taper from their corresponding first end 40 towards their corresponding second end 42. The narrowing width $W_3$ of housing 72 may be complementary to the narrowing width of each docking station 18. Thus, housing 72 may have a shape which is complementary to a shape of each of docking stations 18 as well as docking station 32, as further described herein. The narrowing taper of housing 72, in combination with key 80, may define an external contour of housing 72 which is adapted to mate with an internal contour of battery docking stations 18 and 32. The shape and contour of housing 72 can enable battery assembly 16 to engage snugly in docking stations 18 or in docking station 32, when inserted in one orientation.

Figure 6:
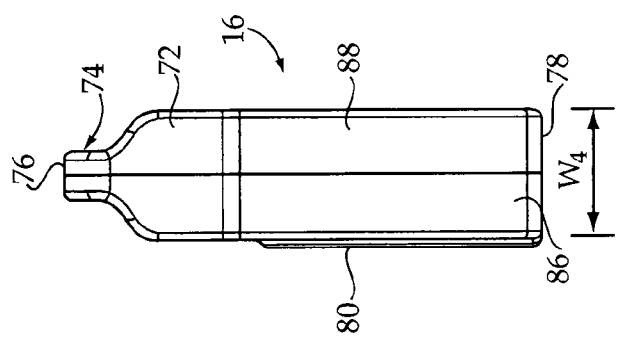
FIG. 6 is a side view also in elevation of the power supply unit of FIG. 5.
Figure 7:
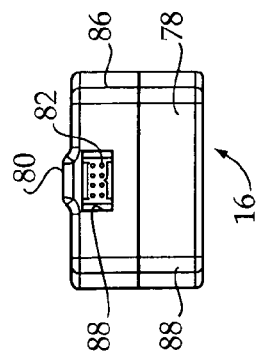
FIG. 7 is an end view also in elevation of the power supply unit shown in FIGS. 5 and 6.

Turning now to FIG. 6, there is shown a side view of battery assembly 16, illustrating the protruding configuration of key 80, as well as a width dimension $W_4$ of housing 72 which comprises a uniform width dimension. It may also be noted that housing 72 has a first housing piece 86 whereupon key 80 is located, and a second housing piece 88. Together, housing pieces 86 and 88 comprise a clamshell configuration for housing internal components of battery assembly 16, as further described and illustrated herein. Referring also to FIG. 7, there is shown an end view of battery assembly 16, specifically of second end 78. It may be noted that first housing piece 86 includes an aperture 84 formed therein. An electrical connector 82, for example, comprising a pin-type connector such as an eight-pin connector, may be positioned to align with aperture 84, and may be slightly recessed from aperture 84 in certain embodiments. Electrical connector 82 might comprise either of a male connector or a female connector. Electrical connector 82 may be configured to couple with battery charging interfaces 19, as well as with battery input interface 33 of battery docking station 32, as further described herein. In one embodiment, two of the eight pins of electrical connector 82 may correspond to a positive terminal of a battery housed within housing 72, and two other pins may correspond to a negative terminal of the battery housed within housing 72. One of the eight pins may correspond to a thermistor of battery assembly 16 to enable temperature monitoring. One other pin of the eight pins may comprise a battery detection pin to enable detection of electrically connecting battery assembly 18 with battery input interface 33 or one of battery charging interfaces 19. The remaining two pins may comprise data communication connectors, with a first one of the pins comprising a clock line and the second one of the pins comprising a data communication link such that communications between battery assembly 16 and a non-resident microprocessor, for example, can take place serially in a manner analogous to other serial communications configurations known from the electronics arts.

Figure 8:
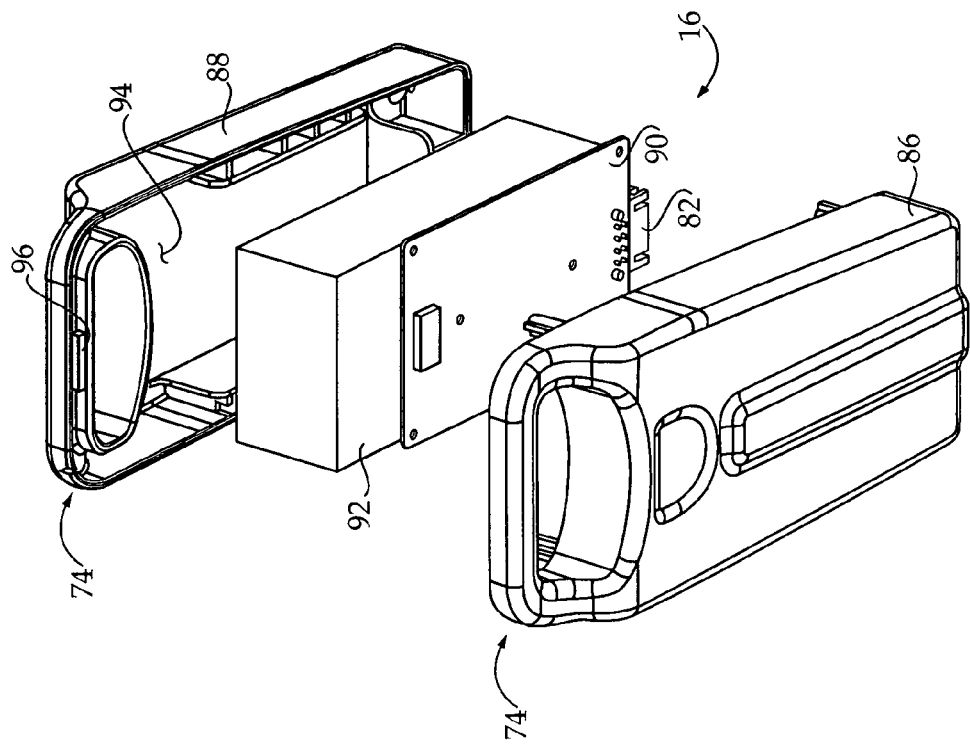
FIG. 8 is an exploded view of the power supply-unit shown in FIGS. 5-7.

Referring now to FIG. 8, there is shown an exploded view of battery 16 illustrating the described clamshell configurations of housing pieces 86 and 88 as well as an interior space 94 defined by housing pieces 86 and 88. An electrical energy device comprising a battery 92, and a control board 90 may be positioned in space 94. A variety of electronic components may be mounted on control board, such as a memory, a microprocessor and one or more communication and power buses. Such components are described in more detail in connection with the description hereinbelow of the use of battery assembly 16 in power system 28. Also illustrated in FIG. 8 is a sensor 96, which is positioned within handle 74 and is configured to detect user interaction with handle 74. In one embodiment, sensor 96 may comprise a touch sensor or a non-touch sensor which senses user contact with a sensing interface of sensor 96 or user proximity to a sensing interface of sensor 96, respectively, which is in turn indicative of user interaction with battery assembly 16. One example embodiment could employ a TS100 sensor available from TouchSensor Technologies of Wheaton, Ill. A variety of known thermal sensors might be used in another embodiment to enable detection of a user's hand in contact with or proximity to handle 74 by way of detecting body heat from the user's hand.

Mounting a sensor 96 in or on housing 72 is contemplated to be one practical implementation strategy, however, the present disclosure is not thereby limited. In other embodiments a different type of detector or a detector mounted in a different location than that disclosed herein might be used to determine user proximity or user interaction with battery assembly 16. For example, a mechanical switch might be coupled with battery assembly 16, or alternatively coupled with docking station 32, to enable detection of user interaction with battery assembly 16. In a mechanical switch embodiment, a switch could be used which has a movable switching element that is moved during undocking battery assembly 16. The movable switching element might establish an electrical connection, break an electrical connection, or change the voltage, resistance or current, etc., associated with an electrical connection to indicate user interaction with battery assembly 16. In still other embodiments, a detector configured to "detect" user interaction with battery assembly 16 might comprise a user-actuated detector separate from either of battery assembly 16 or docking stations 18 or 32. In other words, a user might manually actuate a button or switch prior to or during undocking battery assembly 16 to communicate to a control device that user interaction is taking place. One application for detecting user interaction with battery assembly 16, via any of the embodiments described herein, is contemplated to be detecting a user grasping handle 74 during swapping battery assembly 16 when docked with a mobile workstation with a substitute battery assembly. This can enable power system 28 to switch from a first power sourcing mode to a second power sourcing mode, as further described herein.

Figures 9, 10:
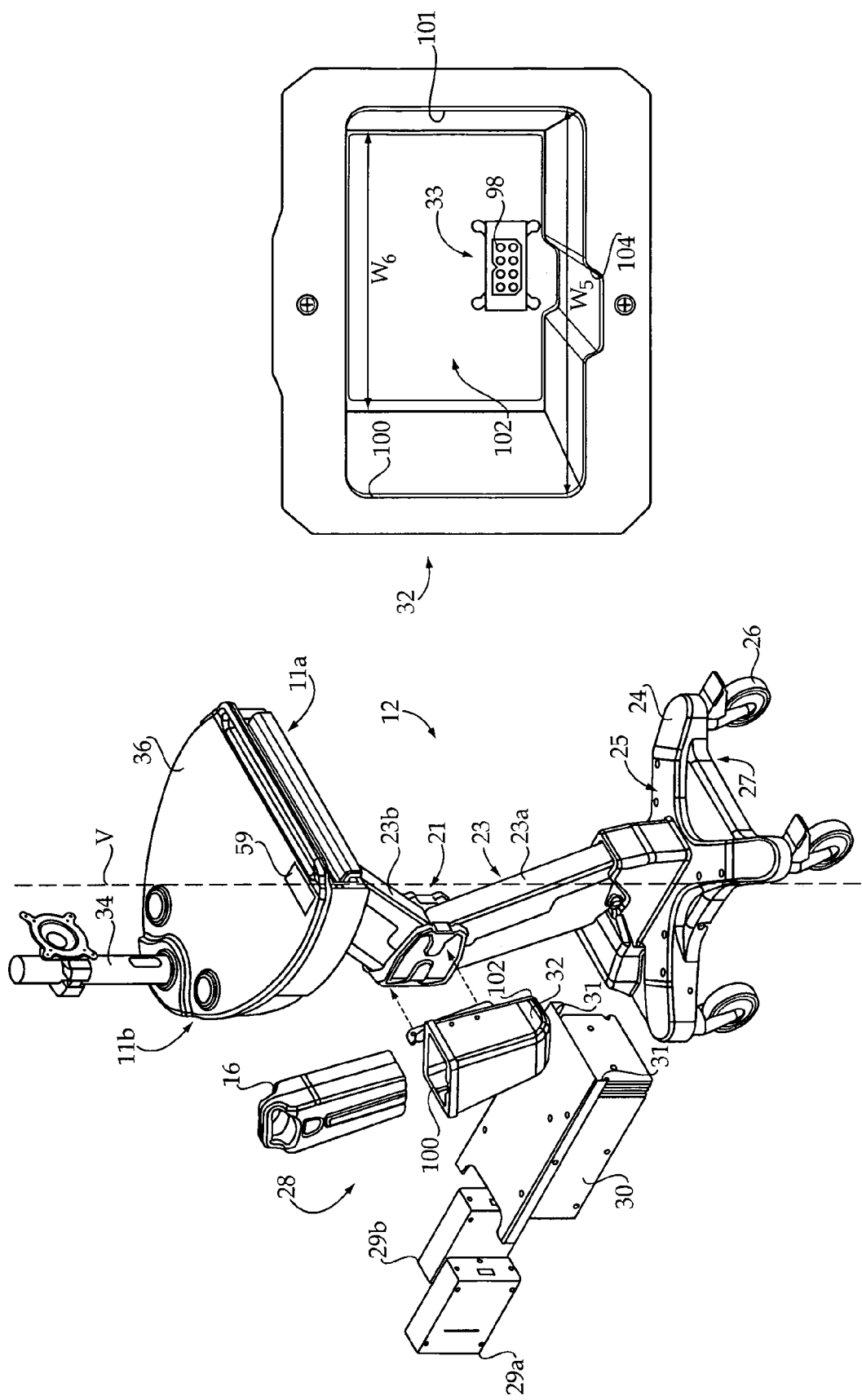
FIG. 9 is a pictorial view of a mobile workstation according to one embodiment.
FIG. 10 is an end view in perspective of a battery docking station according to one embodiment.

Turning now to FIG. 9, there is shown a workstation 12 similar to workstations 12a and 12b shown in FIG. 1 and thus described by way of identical reference numerals. The present description of workstation 12 should thus be understood to refer to either of workstations 12a and 12b of system 10, although as mentioned above it should be appreciated that workstations 12a, 12b comprising system 10 might differ from one another in certain embodiments. Thus, the present description should not be understood as limiting, but illustrative only. In one embodiment, support arm assembly 23 may include a lower arm 23a and an upper arm 23b. A pivot assembly 21 may be coupled with upper and lower arms 23a and 23b to allow a vertical position of work platform 36 to be varied in a known manner. A connection between lower arm 23a and base 24 might also comprise a pivoting connection in certain embodiments.

Also shown in FIG. 9 is a display 59, which may be an LCD display or the like mounted on or in work platform 36, and configured to display information relating to status and operation of power system 28, as further described herein. Battery assembly 16 is also shown in FIG. 9, removed from docking station 32. The following description of battery assembly 16 with respect to workstation 12, and in particular docking station 32, should be understood as applicable to any of the battery assemblies of set 13 described above. The present description of docking station 32 should likewise be understood to be generally applicable. Docking station 32 may have a first, open end 100 and a second, blind end 102. In one embodiment, docking station 32 may comprise a holster configured to mount to pivot assembly 21 in an exposed and readily accessible location. Workstation 12 may define a vertical axis V, which extends through lower side 27 and upper side 25 of base 24. It may be noted that work platform 36 is supported via upper arm 23b at a location vertically above base 24. The mounting location of docking station 32 on pivot assembly 21 may be at a location which is vertically between base 24 and work platform 36, as also shown in FIG. 1 in connection with workstation 12a. Also shown in FIG. 9 are certain of the subcomponents of power system 28, including control system housing 30, which may have mounting rails 31 for mounting at a location at lower side 27 of base 24. Power system 28 may also include one or more auxiliary power output modules 29a and 29b which are configured to be positioned within housing 30, and thus also mounted at lower side 27.

Turning now to FIG. 10, there is shown docking station 32 viewed from its first, open end 100 towards its second, blind end 102. It will be noted that docking station 32 has certain similarities with docking stations 18, described above, and may be substantially identical in shape and internal contour in at least certain embodiments. Docking station 32 may include an inner diameter 101 defining a guide adapted to guide battery assembly 16, or a battery assembly which is interchangeable with battery assembly 16, during docking with docking station 32. Docking station 32 may also include a key 104 also defined by inner diameter 101, comprising for example an involute flute, which extends from first end 100 towards second end 102. Docking station 32 may also have a first width dimension $W_5$ at first end 100, and a second, smaller width dimension $W_6$ at second end 102. Docking station 32 thus has a narrowing taper from first end 100 towards second end 102. An internal height of docking station 32, the dimension perpendicular widths $W_5$ and $W_6$, may be uniform from first end 100 to second end 102. It will be recalled that housing 72 of battery assembly 16 also may have a narrowing taper. Housing 72 may also have a shape complementary to a shape of inner diameter 101 of docking station 32. Housing 72 also has an external contour which is configured to mate with an internal contour guide defined by inner diameter 101.

It may further be noted that inner diameter 101 has a non-polygonal shape and an internal contour which corresponds with the non-polygonal shape over at least a portion of a distance from first end 100 to second end 102. Housing 72 may have a complementary non-polygonal shape, and an external contour matched to the internal contour of the guide defined by inner diameter 101 and configured to mate therewith during docking battery assembly 16 in docking station 32. Returning to FIG. 9, docking station 32 is shown approximately in an orientation it may occupy when mounted on support arm assembly 23. Thus, open end 100 is positioned vertically higher than blind end 102. This orientation enables gravity assisted drop-in engagement of battery assembly 16 in docking station 32. Mounting docking station 32 in an exposed location on a side of support arm assembly 23 and in the described orientation will allow personnel to readily decouple battery assembly 16 from docking station 32, and readily drop in a substitute battery assembly, minimizing interruptions in work and use of mobile workstation 12. The described mounting location, orientation and configuration of docking station 32 further allows docking station 32 to function as a holster, such that it can be accessed from a direction which is not obstructed by other components of workstation 12. A user will typically utilize workstation 12 from a front side 11a, and will typically access battery docking station 32 from an opposite back side 11b, which represents an access path and direction to docking station 32 in three-dimensional space which is relatively less obstructed than other access paths or directions. As shown in FIG. 10, battery input interface 33 may be located at blind end 102, and may include an electrical connector 98 which is configured to electrically connect with electrical connector 82 of battery assembly 16 such that an electrical power link, and also a communication link, may be established between battery assembly 16 and power system 28 upon docking of battery assembly 16 in docking station 32. When battery assembly 16 is decoupled from docking station 32, the electrical power and communication links between battery assembly 16 and power system 28 may be disconnected.

By implementing the concepts described herein, mobile workstation 12 may power a computerized device of workstation 12 such as device 38, or another computerized device, with a removable battery, represented by battery assembly 16a in FIG. 1. When battery assembly 16a is to be swapped out, a user may decouple removable battery 16a from docking station 32, and dock a substitute battery assembly represented by battery 16b in FIG. 1 in the guide defined by inner diameter 101 of battery docking station 32 at a location between base 24 and computerized device 38. When the substitute battery assembly 16b is docked with battery docking station 32, computerized device 38 may be powered with battery assembly 16b. The batteries disclosed and described herein may comprise relatively lightweight batteries such as lithium polymer batteries, having a power to weight ratio of about five Amp-hours per pound or greater. Many earlier designs utilized relatively heavy lead-acid batteries, having power to weight ratios of about five to ten times less than that of the lithium polymer batteries which may be used as described herein. Even where conventional batteries could be considered removable, they were typically unwieldy and even dangerous to manipulate by personnel.

Figure 11:
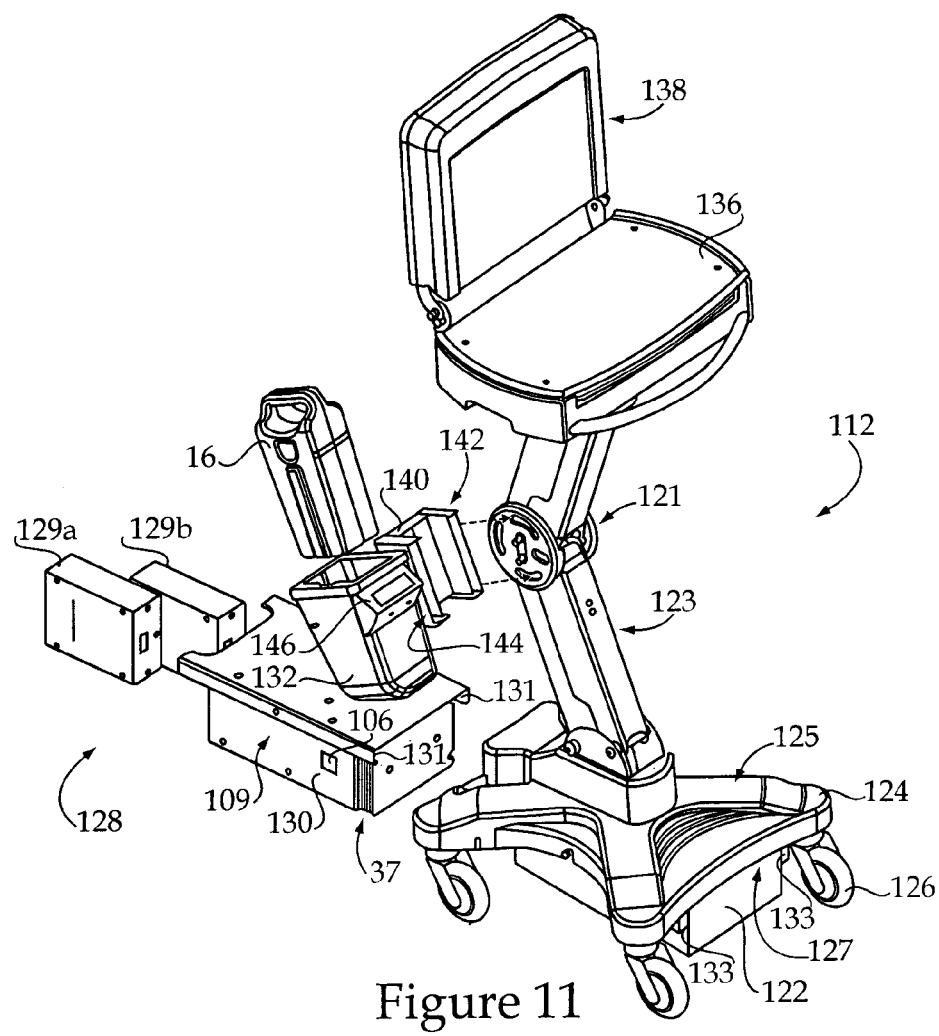
FIG. 11 is a pictorial view of a mobile workstation and power system retrofit kit according to one embodiment.
Figure 12:
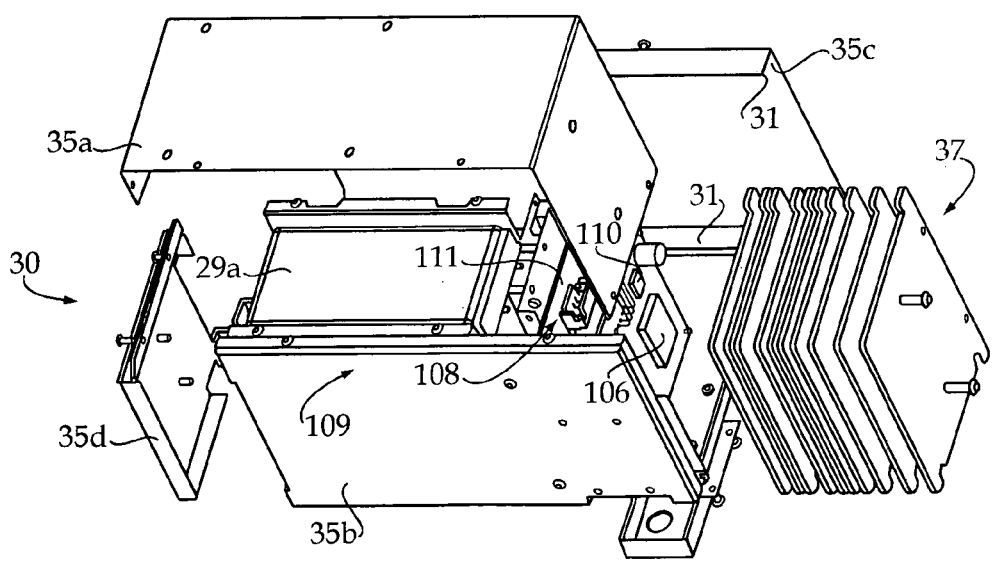
FIG. 12 is an exploded view of a portion of a power system according to one embodiment.

Referring now to FIG. 12, there is shown an exploded view of housing 30 also illustrating certain of the components of control system 109 which may be positioned therein. Housing 30 may in some embodiments be identical to housing 130 shown in FIG. 11 and described below, hence the present description of housing 30 should also be understood to refer to components of housing 130. Housing 30 may include a plurality of housing panels, including a side panel 35a, a top panel 35c which includes rails 31, a bottom panel 35b and an end panel 35d. Certain of the components of control system 109 may be housed within housing 30, including a control module 108 having a main control board 111, and an electronic control unit such as a microprocessor 110 coupled with control board 111. Back-up battery 106 is also shown positioned in housing 30 and mounted on control board 111. The auxiliary power output modules, one of which is shown, 29a, may also be positioned within housing 30 and may be electrically connected with control module 108. Ballast 37, for example comprising a plurality of ballast plates, may also be coupled with or positioned within housing 30 to assist in positioning a center of gravity of a workstation to which housing 30 is coupled at a desired location.

Figure 13:
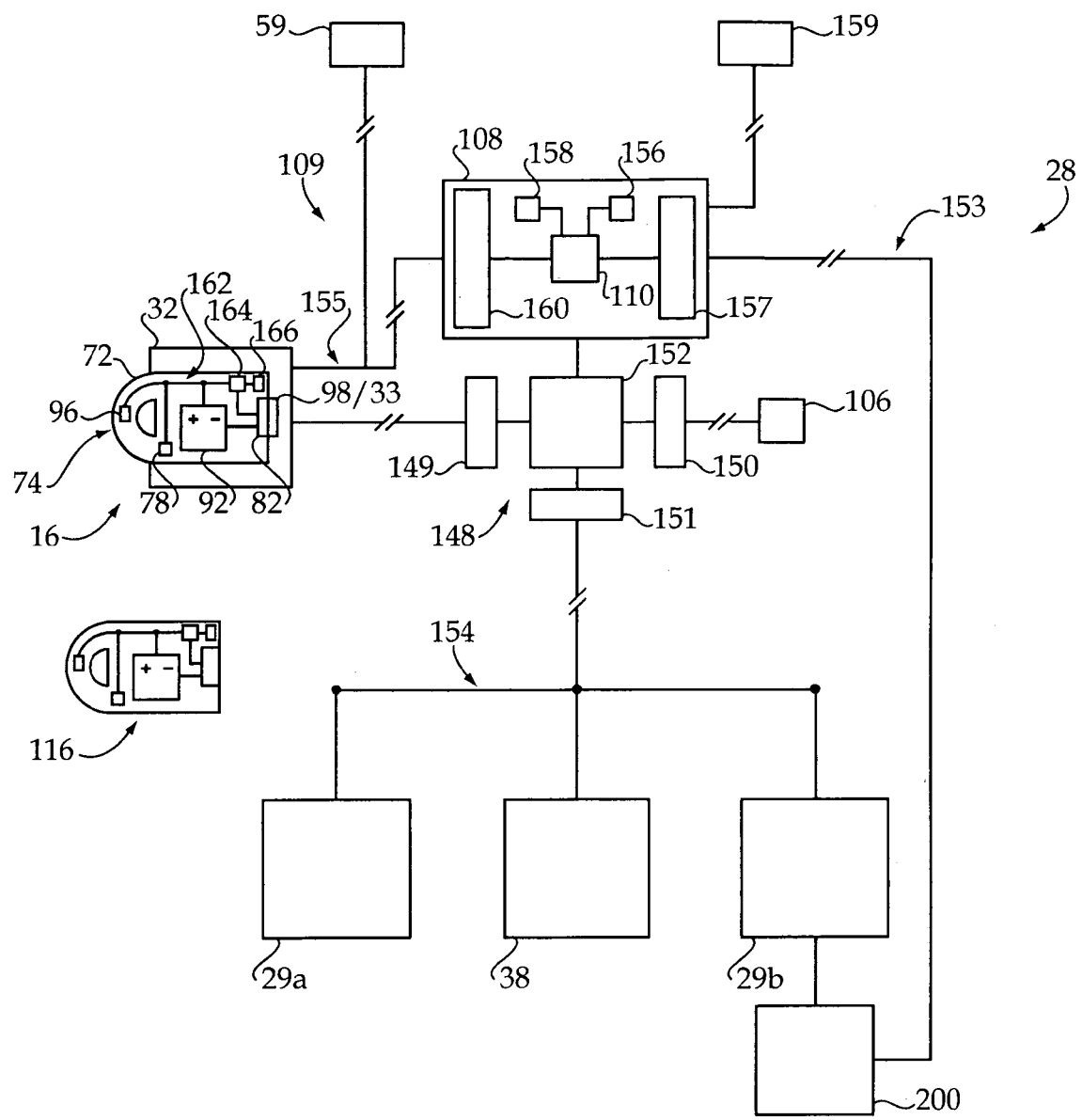
FIG. 13 is a block diagram illustrating a power system and control system according to one embodiment.

Turning to FIG. 13, there is shown a schematic illustration of power system 28 by way of a block diagram. Power system 28 may include battery docking station 32, shown having a first removable battery assembly 16 docked herewith. A second removable battery assembly 116, which is interchangeable with battery assembly 16, and may be identical to battery 16, is also shown in FIG. 13. It will be recalled that battery assembly 16 may include a plurality of components housed with housing 72. In the embodiment shown in FIG. 13, battery assembly 16 includes an electrical energy device having a battery 92, electrically connected with electrical connector 82. Battery assembly 16 is shown as it might appear when electrically connected with electrical connector 98 of battery input interface 33 of battery docking station 32 via electrical connector 82. Battery assembly 16 may also include sensor 96, which is in communication with a microprocessor 164 resident on battery assembly 16 via a communication bus 162 comprising, for example, a smart management bus.

A memory 166 is also coupled with microprocessor 164. It will be recalled that battery assemblies according to the present disclosure may include a charging cycle counter. Accordingly, in one embodiment battery assembly 16 may include a charging cycle counter which comprises microprocessor 164 and memory 166 and stores a charging cycle count for battery assembly 16. Thus, memory 166 may comprise a rewritable memory such that microprocessor 166 can store charging cycle count date and other data thereon. Display 78, or another indicating device, is also shown connected with microprocessor via communication bus 162. In one embodiment, display 78 may comprise a push-on fuel gauge configured to display a power level remaining in battery 92 in response to being actuated by a user. As shown in FIG. 13 battery assembly 16 is docked with docking station 32 such that it is electrically connected with power system 28, and also in communication with power system 28. Battery assembly 16 may thus be understood to include a segment of a power supply circuit connecting battery 92 with power system 28, as well as a segment of a communication link from sensor 96, and each connecting with electrical connector 82.

Docking station 32 may be electrically connected with a power interface 148 of power system 28, which includes a first input interface 149 comprising a power link between docking station 32 and power interface 148. Thus, connecting battery assembly 16 with electrical connector 98 of docking station 32 establishes a power link between battery assembly 16 and power system 28. Power interface 148 may further include a second input interface 150 which is electrically connected with back-up battery 106, and an output interface 151 which is electrically connected with a power bus 154. Computerized device 38 may be coupled with power bus 154, as may first and second auxiliary power output modules 29a and 29b. It should be appreciated that the illustrated configuration is in many respects purely illustrative, and multiple power buses, power output modules, DC to DC converter modules, etc. might be used without departing from the scope of the present disclosure. In one embodiment, power module 29a may comprise an AC power output module configured to supply power from power bus 154 to an AC powered peripheral device (not shown). Power output module 29b may comprise a DC output module which is configured to supply power to a DC peripheral device 200.

Power system 28 may further include control system 109, comprising control module 108. Control module 108 may include microprocessor 110, a memory 156 coupled with microprocessor 110 which may comprise a rewritable memory, and a countdown timer 158 also connected with microprocessor 110. Control module 108 may further include a first data interface 106 which connects a communication link 155 with microprocessor 110. Communication link 155 may connect docking station 32 with data interface 160, such that data associated with battery assembly 16 may be communicated to microprocessor 110. In one embodiment, communication link 155 may communicate a user interaction signal from sensor 96 to microprocessor 110 which is indicative of user interaction with battery assembly 16. In this manner, when a user grasps battery assembly 16 via handle 74, sensor 96 may output a signal which is communicated to microprocessor 110. First date interface 160 may thus be understood also as a detector interface, as signals from sensor 96 or another type of detector may be received therewith to indicate user interaction with battery assembly 16. In still other embodiments, the absence of a signal via interface 160 could be indicative to microprocessor 110 that a user is interacting with battery assembly 16, or a change in a signal value, etc.

Control module 108 may further include a second data interface 157 which is coupled with another communication link 153 connecting control module 108 with peripheral device 200. Display 59 may also be coupled with microprocessor 110 via communication link 155. It should be appreciated that while communication link 155 will typically be a wired communication link, as will the other communication links described herein, in other embodiments wireless communication might be used. Power system 28 may further include a programming interface 159 coupled with control module 108 which is configured for downloading updated programming software to control module 108 for storing on memory 156. For example, as changes or additions are made to power system 28 or to an associated workstation, such as addition of peripheral devices or substitution of components, software or firmware updates may be enabled by overwriting or supplementing computer executable control system instructions recorded on memory 156.

Power system 28 may be configured to operate in a first power sourcing mode where power interface 148 receives power via input interface 149 from docking station 32, and supplies the electrical power via output interface 151 to power bus 154. In other words, in the first power sourcing mode, power may be received via input interface 149 from battery assembly 16. Power system 28 may be further configured to operate in a second power sourcing mode where power interface 148 receives power via input interface 150 from back-up battery 106, and supplies the power via output interface 151 to power bus 154. In one embodiment, in the first power sourcing mode or via a sub-routine associated with the first power sourcing mode, back-up battery 106 may be recharged by electrically connecting back-up battery 106 with battery assembly 16 via power interface 148, as further described herein.

Power interface 148 may further include a switching device 152, such as a solid state transistor switch, which is configured to switch power interface 148 from the first power sourcing mode to the second power sourcing mode, responsive to detecting user interaction with battery assembly 16. In other words, switching device 152 may be configured to switch power system 28 from a state in which battery assembly 16 supplies power to power bus 154 to a state in which back-up battery 106 supplies power to power bus 154. In other embodiments, switching device 152 might be configured to switch power system 28 from a first mode receiving power from battery assembly 16 to a second mode receiving power from a second battery assembly which is different from back-up battery 106, such as a second removable battery assembly docked with a second docking station (not shown) of power system 28.

In one embodiment, control module 108 may be configured via software and/or firmware to control switching between the respective power sourcing modes. To this end, memory 156 may store computer executable instructions for controlling power sourcing via control system 109. Microprocessor 110 may in turn be configured by way of executing computer executable instructions stored on memory 156 to switch power interface 148 from the first power sourcing mode to the second power sourcing mode. It is contemplated that one practical implementation of the described control strategy will be switching power system 28 to a back-up mode while battery assembly 16 is swapped with a substitute battery assembly such as battery assembly 116. Battery assembly 16 may be decoupled from docking station 32 at a first time, and battery assembly 116 may be docked with docking station 32 at a second time. Back-up battery 106 may provide electrical power to power system 28 between the first time and the second time. When battery assembly 116 is substituted for battery assembly 16, control system 109 may detect electrical connection of battery assembly 116 via electrical connector 98 and responsively switch power system 28, or more specifically power interface 148, back to the first power sourcing mode. It will be recalled that electrical connector 98 may comprise a multi-pin connector configured for serial communication. One of the pins associated with electrical connector 98 may be a pin dedicated at least in part to enabling detection of battery assembly 16, 116 by microprocessor 110 when docked in docking station 32.

It will be recalled that display 59 may be configured to display various sorts of information associated with power system 28. In one embodiment, display 59 may display information in a first display mode relating to charge state, or various other data associated with battery assembly 16, communicated to display 59 from battery assembly 16 via communication link 155. Data associated with battery assembly 16 may also be communicated to microprocessor 110 from communication link 155 by way of data interface 160. When battery assembly 16 is decoupled from docking station 32, microprocessor 110 may switch display 59 to a second display mode to display other information, as described herein. In one example embodiment, decoupling of battery assembly 16 from docking station 32 may induce microprocessor 110 to activate countdown timer 158. In parallel or following activating countdown timer 158, microprocessor 110 may switch display 59 to the second display mode comprising a timing mode where it can display a countdown time as dictated by countdown timer 158, and further described herein. Switching display 59 between its respective display modes may take place responsive to a user interaction signal received via data interface 160. When countdown timer 158 has expired, microprocessor 110 may initiate a shutdown mode, whereby power system 28 is powered down. The shutdown mode and different display modes may be enabled by computer executable instructions stored on memory 156, as further described herein. When countdown timer 158 is deactivated prior to expiring, such as where a replacement battery is docked with docking station 32 prior to expiration of countdown timer 158, a shutdown signal for power system 28 and an associated workstation will typically not be generated.

It will be recalled that sensor 96 may comprise a user proximity sensor. This means that sensor 96 may have a first output state or a normal use state, and a second output state comprising a user proximity state, for example where a user is grasping or is in proximity to handle 74. As described, sensor 96 may output a user interaction signal via communication link 155 which is received by microprocessor 110 and indicates that user interaction with battery assembly 16 has been detected. Microprocessor 110 may output a power source switching signal to power interface 148 to switch from the first power sourcing mode to the second power sourcing mode in response to detecting user interaction with battery assembly 16. One advantage of the present disclosure is that power may be continuously supplied to power bus 154 while a user swaps battery assembly 16 with substitute battery assembly 116. In other words, when no battery is docked in docking station 32, the second power sourcing mode may be used to supply power to power bus 154 from back-up battery 106. This strategy is enabled in part by the ability of sensor 96 to detect user interaction with battery assembly 116 in advance of electrically disconnecting battery assembly 16 from docking station 32. In other words, sensor 96 may output a user interaction signal prior to electrical connectors 82 and 98 being electrically disconnected from one another, and thus prior to completing decoupling battery assembly 16 from docking station 32.

Microprocessor 110 may thus switch power interface 148 between its power sourcing modes such that seamless power supply to power bus 154 is possible. Thus, when a user brings a workstation such as workstation 12a, 12b, 12 to battery charging system 14, it is not necessary to power down the associated workstation to swap out the primary battery. In a further aspect, the described configuration for battery assembly 16, the configuration, location and orientation of docking station 32 and the use of a relatively light weight battery allows battery swapping to be relatively fast and simple. Even in earlier designs where a battery assembly might be considered removable, the relatively heavy weight of conventional batteries and the lack of a facile docking and undocking strategy prevented switching batteries from taking place in an optimal and convenient manner. A further advantage over state of the art systems is obviating the need to ever plug a workstation into a wall outlet, either for recharging a resident battery or while swapping removable batteries. Accordingly, a fleet of mobile workstations, such as are shown in FIG. 1 may be completely separate from a facility's native power system apart from battery charger 15. This provides improvements not only in efficiency and reliability, but also safety as the interaction of personnel with electrical outlets during using workstations as described herein is eliminated.

Figure 15:
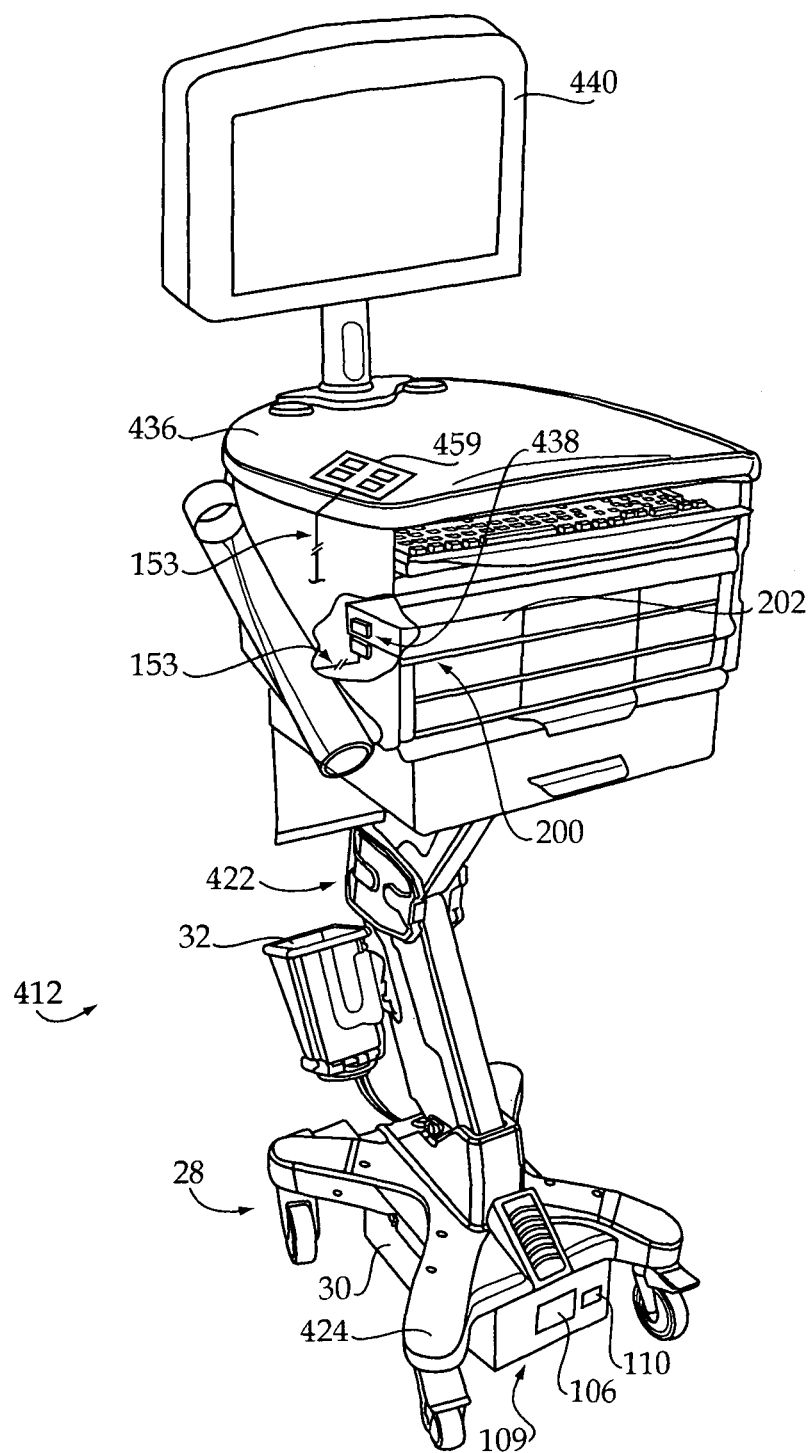
FIG. 15 is a diagrammatic view of a mobile workstation according to one embodiment.

A further aspect of the present disclosure relates to the manner in which peripheral devices for a mobile workstation may be powered and controlled. Referring also to FIG. 15, there is shown a mobile workstation 412 according to one embodiment. Mobile workstation 412 may include a variety of features similar to features of the other workstations described herein, including a frame 422 having a support arm assembly, a base 424 and a work platform 436. A computerized device 440, such as a computer having a display and a memory (not shown), may be mounted at a position vertically above base 424, similar to computerized device 38 shown in FIG. 1. Workstation 412 may further include a power system 28 having a battery docking station 32, and a control system 109 positioned within a control system housing 30 mounted under base 424. Apart from certain aspects of the software and/or firmware used in operating and controlling power system 28, power system 28 may be substantially as described in connection with FIG. 13. Hence, identical reference numerals are used for certain of the components of workstation 412 in FIG. 15.

Power system 28 may further include a back-up battery 106 and a microprocessor 110, and control system 109 may be configured to control power sourcing between back-up battery 106 and a removable battery docked with battery docking station 32 in a manner similar to that described in connection with the foregoing embodiments, and therefore not further specifically described herein. Mobile workstation 412 may also include a peripheral device 200 mounted to frame 422. Peripheral device 200 may comprise any of a wide variety of known and even yet to be developed devices. For instance, peripheral device 200 might comprise a data gathering device such as an electronic scanning device, a blood pressure monitor, a thermometer, an EKG device, etc. Peripheral device 200 might also comprise a variety of other devices unrelated to gathering data, such as a vacuum, an electrical motor for propelling workstation 412 or for raising or lowering work platform 436, etc.

In one embodiment, peripheral device 200 may comprise an electronically controlled device 438 having a locked state and a use state. Device 200 might thus be a piece of equipment which may be locked against unauthorized or inappropriate use. In one further embodiment, electronically controlled device 438 may comprise an electrically actuated device such as a motor, an actuator or an electronically operated lock having a locked state and an unlocked state. In one example, electronically controlled device 438 may be used to control access to one or more medication drawers 202. A communication link 153 may be provided which connects electronically operated lock 438 with microprocessor 110, as also shown in the block diagram of FIG. 13. Workstation 412 may still further include a user interface 459 which also connects with communication link 153. In one embodiment, user interface 459 may comprise a keypad configured such that a user can enter an access code or the like, which may be communicated as data inputs to microprocessor 410 via communication link 153 and data interface 157, as shown in FIG. 13. Microprocessor 110 may output an unlocking control signal to electronically operated lock 438 if the data inputs meet a predetermined criterion, such as matching an access code stored in memory 156. When lock 438 is unlocked, the associated drawer 202 may be opened to allow access to medications stored therein. When drawer 202 is closed, microprocessor 110 may automatically return device 438 to its locked state. If drawer 202 remains open longer than a specified time, microprocessor 110 could output an alert signal or the like. Countdown timer 158 could be used in connection with such a feature.

Workstation 412 differs, among other things, from earlier mobile workstations in that power system 28, which is resident on mobile workstation 412 and is separate from and operable independently of computerized device 440 and peripheral device 200, may control both power sourcing and data processing. In other words, power system 28 may by way of control system 109 be configured to control power to a plurality of separate computerized devices such as device 440 and device 200 coupled with power system 28, while also functioning to process data in one or more of the separate computerized devices.

This differs from earlier workstations where peripheral devices either needed to be controlled by their own data processing system, or relied upon control via a primary computer of the mobile workstation. Thus, power system 428 may be thought of as an intelligent power system which includes both power sourcing control capability, and data processing capability. This is contemplated to free up a primary computer, such as computerized device 440, to perform native hospital or clinic functions and solely run native hospital or clinic software. Data processing and/or control over a peripheral device can thus be separated entirely from operation of the primary computer. The present description of power system 28 being resident on, separate from and operable independently of computerized device 440 is intended to mean, among other thins, that power system 28 is a part of workstation 412 itself, at least in the FIG. 15 embodiment. Thus, another peripheral device, or even a second computer placed on workstation 412 in addition to computerized device 440, would not be fairly said to be resident on workstation 412, separate from, and operable independently of the plurality of computerized devices represented by devices 200 and 440.

Returning to FIG. 13, it will be recalled that microprocessor 110 may receive data from peripheral device 200. In an embodiment suitable for use in connection with mobile workstation 412, memory 156 may store computer executable instructions comprising a power sourcing algorithm and a data processing algorithm. Microprocessor 110 may be configured by way of executing the power sourcing algorithm to switch power interface 148 from a first power sourcing mode receiving power via first input interface 149 to the second power sourcing mode receiving power via second input interface 150. Microprocessor 110 may further be configured by way of executing the data processing algorithm to control peripheral device 200 in response to inputs received via data interface 157. As described above, user interface 459 may be configured to receive user inputs. In one embodiment, the user inputs might comprise activation data for peripheral device 200, whereas in other embodiments the inputs might comprise deactivation data. For example, activation data might be used where only certain users are authorized to use peripheral device 200, and thus microprocessor 110 only permits activation of peripheral device 200 in certain instances. Deactivation data might be used, for example, in the foregoing electronic lock example to deactivate, e.g. unlock, drawer(s) 202. Microprocessor 110 may be configured by way of executing the data processing algorithm to compare the activation data or deactivation data, or both, with data stored on computer readable memory 156. If activation or deactivation of peripheral device 200 is determined to be appropriate in response to the user inputs, microprocessor 110 may output an appropriate control signal to peripheral device 200.

Referring now to FIG. 11, there is shown a workstation 112 representing an existing workstation which is retrofitted with a replacement power system 128 via a retrofit kit. While it is contemplated that many embodiments of the present disclosure will include workstations purpose built to accommodate the power system and other components described herein, it may be desirable in many instances to retrofit existing workstations with certain of the elements and features disclosed herein. Workstation 112 may include a computerized device 138, for example comprising a computer monitor, a work platform 136, a frame comprising a support arm assembly 123 and a wheeled base 124. Base 124 may include an upper side 125 and a lower side 127. An existing battery assembly 122 is shown coupled at lower side 127 of base 124. In one embodiment, retrofitting power system 128 will include coupling power system 128 with mobile workstation 112 in place of an existing power system, which includes battery assembly 122. Battery assembly 122 may thus represent one of the unwieldy and relatively heavy lead-acid battery assemblies of the prior art.

As mentioned above, retrofitting workstation 112 may take place by way of a retrofit kit. Many different components may be included in a retrofit kit according to the present disclosure. One practical implementation strategy for a retrofit kit will include the components of power system 128 pictured in FIG. 11, recognizing that certain of the components might be excluded or others included without departing from the scope of the present disclosure. The retrofitting method may begin by removing existing battery assembly 122 from a mount 133 defining a first mounting location on workstation 112. A housing 130 for certain components of power system 128, namely, control system components, may then be positioned at the first mounting location and coupled with mount 133 in place of existing battery assembly 122. To this end, housing 130 may include mounting rails 131 which are preconfigured to mount housing 130 with mounts 133. Housing 130 may be similar to housing 30 described in connection with FIG. 12. Power system 128 may also include at least one auxiliary power output module 129*a*, 129*b*, configured to be positioned within housing 130. Many of the control and operational aspects and features of power system 128 may be identical to those of power system 28, described elsewhere herein, and reference is therefore made to the discussion herein of power system 28 for the manner of operation and control of workstation 112 once power system 128 is coupled therewith. Likewise, components of power system 128 may also include components similar to those shown as components of power system 28 in FIG. 13, such as control system 109, back-up battery 106, and microprocessor 110.

Retrofitting power system 128 to workstation 112 may also include establishing a power link between a power interface of power system 128 and a docking station 132 for a removable battery assembly 16 of power system 128. The configuration and operation of the power interface of power system 128 may be similar to that of power system 28, and is thus not specifically described or illustrated herein. Retrofitting power system 128 may also include establishing a communication link between control system 109 and a detector of the replacement power system 128 which is configured to detect user interaction with removable battery assembly 16. The detector may comprise a sensor associated with battery assembly 16, such as sensor 96 discussed above, although alternatives such as mechanical switches are contemplated.

It will be recalled that existing battery assembly 122 may be relatively heavy. Accordingly, when housing 130 is swapped with existing battery assembly 122, a center of gravity of workstation 112 may be changed. Changing the location of the center of gravity may be compensated for by placing a ballast 137, for example a plurality of ballast plates coupled with housing 130, in place of existing battery assembly 122. It will further be recalled that mounts 133 define a first mounting location. When power system 128 is coupled with workstation 112, a docking station 132 may be mounted to support arm assembly 123 at a second mounting location which is vertically between base 124 and computerized device 138. In one embodiment, docking station 132 may be mounted to a pivot assembly 121 of support arm assembly 123. Docking station 132 may further define a guide, similar to the guide defined by docking station 32, which is oriented in a non-horizontal orientation to enable gravity assisted drop-in engagement of battery assembly 16 therein.

Docking station 132 may include a display 146, for example comprising an LCD display, positioned thereon and configured to display data associated with battery assembly 16 similar to that of display 59 described elsewhere herein. A mounting bracket 140 may also be provided which includes a first connecting interface 142 configured to connect with pivot assembly 121, and a second connecting interface 144 which is configured to connect with docking station 132. Mounting docking station 132 to support arm assembly 123 via mounting bracket 140 positions docking station 132 in the described non-horizontal orientation, similar to that described in connection with FIGS. 9 and 10. It will further be recalled that battery assembly 16 may include an electrical connector, similar to that described above. Accordingly, docking battery assembly 16 with docking station 132 may comprise the described establishing of a communication link.

INDUSTRIAL APPLICABILITY

Figure 17:
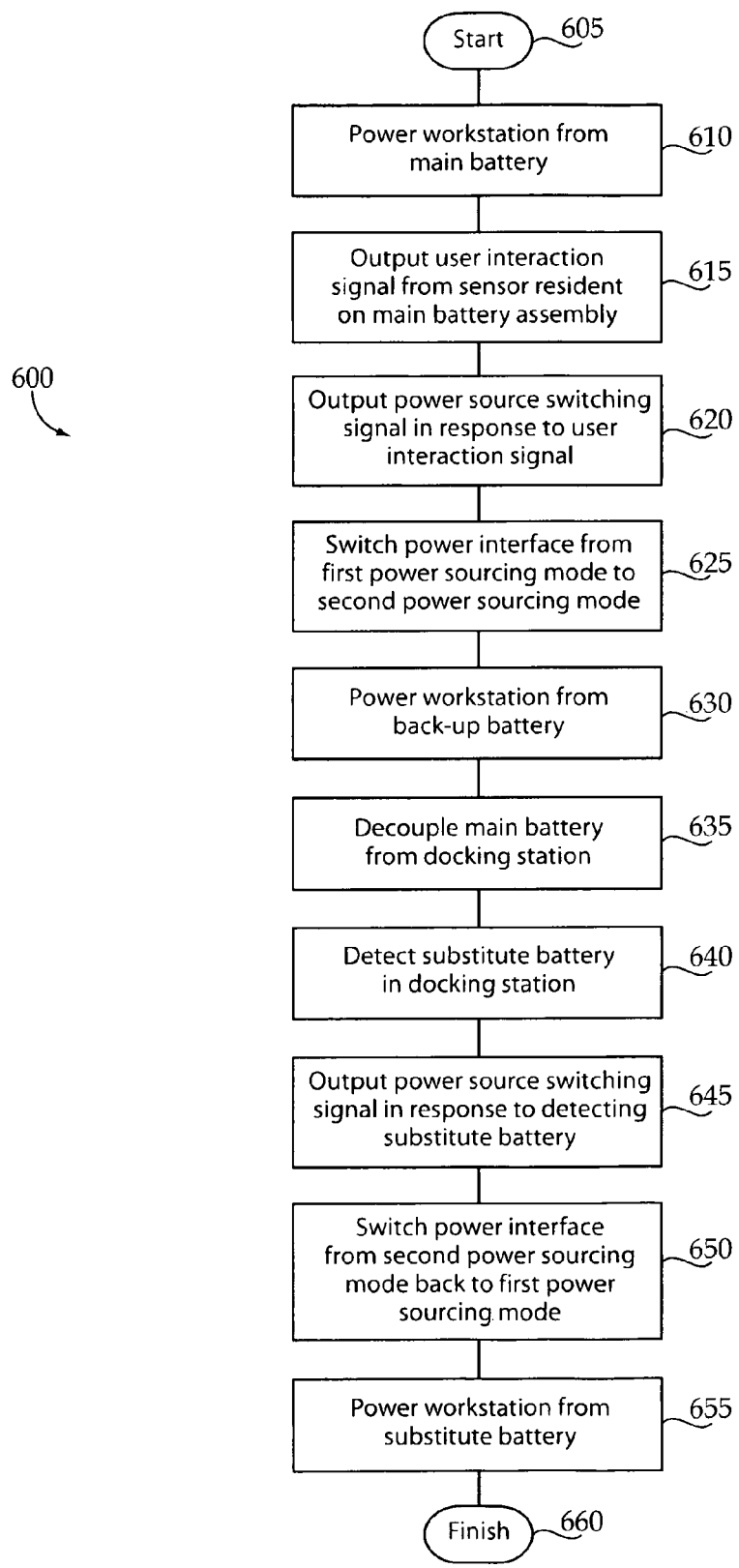
FIG. 17 is a flowchart illustrating a power source switching routine, according to one embodiment.

Referring to FIG. 17, there is shown an example power source switching routine according to the present disclosure by way of a flowchart 600. The process of flowchart 600 may begin at a start, step 605, and may proceed to step 610 where a workstation such as workstation 12a, 12b, 12, 112, 412 is powered via a main battery such as battery 92 of battery assembly 16. At step 610, the workstation, hereinafter referred to as workstation 12, may have battery assembly 16 docked in holster 32. From step 610, the process may proceed to step 615 where sensor 96 may output a user interaction signal. It will be recalled that sensor 96 is resident on battery assembly 16, however, alternatives such as a mechanical switch are contemplated. From step 615, the process may proceed to step 620 where microprocessor 110 can output a power source switching signal in response to the user interaction signal. From step 620, the process may proceed to step 625 wherein power interface 148 is switched from the first power sourcing mode to the second power sourcing mode, responsive to the power source switching signal.

From step 625, the process may proceed to step 630 wherein workstation 12 may be powered from back-up battery 106. From step 630, the process may proceed to step 635 wherein main battery assembly 16 is decoupled from docking station 32. It will be recalled that detecting user interaction will typically take place in advance of electrically disconnecting battery assembly 16 from docking station 32.

From step 635, main battery assembly 16 may be swapped with a substitute battery assembly such as battery assembly 116, which is then docked in docking station 32, and detected in docking station 32 in step 640. From step 640, the process may proceed to step 645 where microprocessor 110 may output another power source switching signal in response to detecting the substitute battery. It will be recalled that one of the electrical connector pins of electrical connector 82 may comprise a detection pin, such that coupling of substitute battery assembly 116, or any of the other interchangeable batteries described herein, may be detected. From step 645, the process may proceed to step 650 where power interface 148 is switched from the second power sourcing mode back to the first power sourcing mode, in response to the power source switching signal. From step 650, the process may proceed to step 655 where workstation 12 is powered from the substitute battery 116. From step 655, the process may proceed to step 660 to finish.

Figure 14:
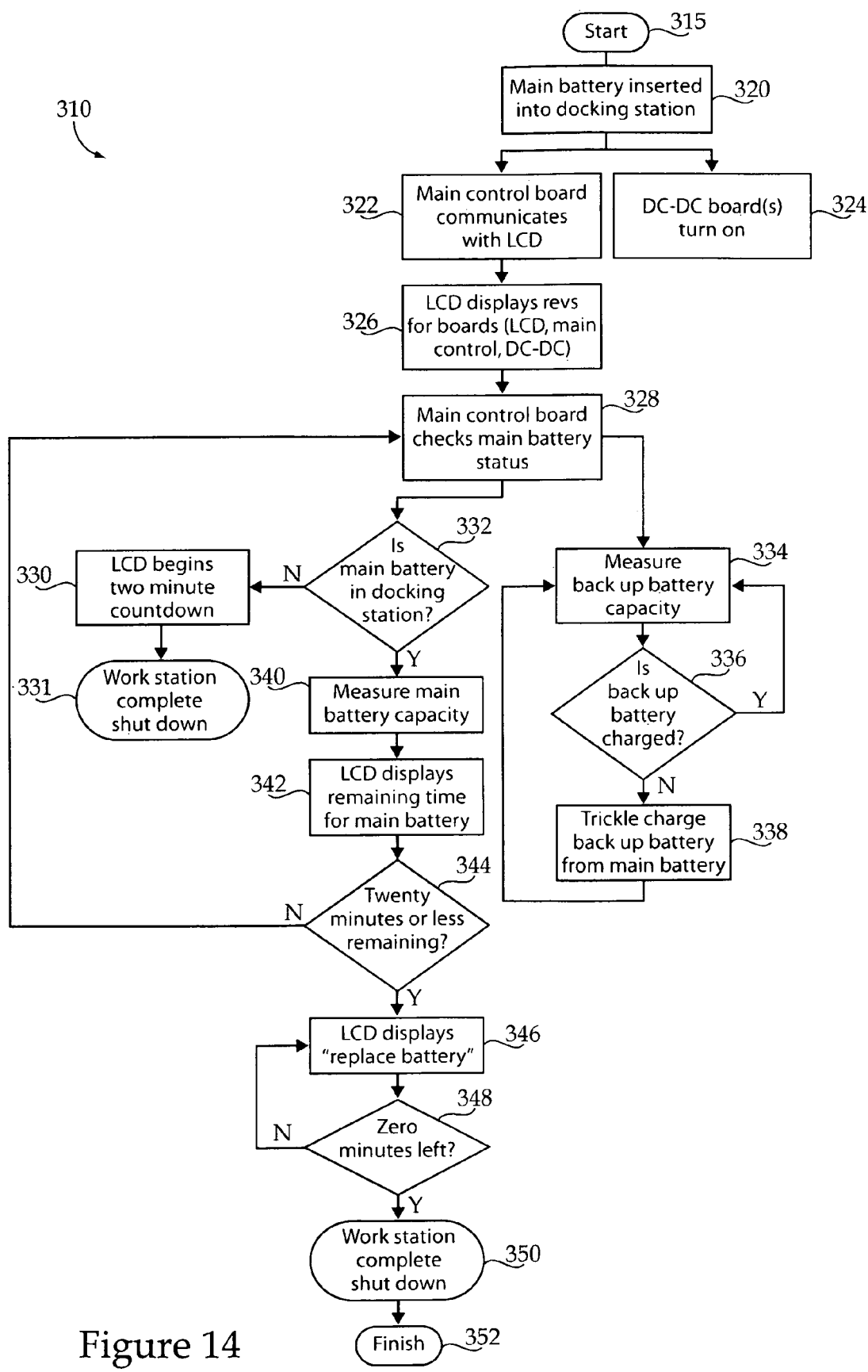
FIG. 14 is a flowchart illustrating operation of the power and control systems of FIG. 13 according to one embodiment.

Turning to FIG. 14, there is illustrated by way of another flowchart 310 an exemplary process for operating and/or using and controlling various of the components of power system 28. It should be appreciated that the process of flowchart 600, described above, may take place in parallel with the process of flowchart 310, or might be a sub-routine of the process of flowchart 310. The process of flowchart 310 may begin at a start, step 315, and may then proceed to a step 320 where a main battery such as that of battery assembly 16 is inserted into docking station 32. From step 320, the process may proceed in parallel to steps 322 and 324. In step 324, DC-DC boards of power system 28 may be turned on, such as a DC-DC board for powering computerized device 38, and DC-DC boards associated with one or more of modules 29a and 29b. In step 322, the main control board, such as control board 111, may communicate with LCD display 59.

From step 322, the process may proceed to step 326 where display 59 displays the software or firmware revisions running for each of the various control boards of power system 28. From step 326, the process may proceed to step 328 where the main control board 111 checks main battery status, such as for battery assembly 16 in the FIG. 13 illustration. From step 328, the process may proceed in parallel to step 332 and 334. In step 334, a capacity of back-up battery 106 may be measured. From step 334, the process may proceed to step 336 to query whether back-up battery 106 is charged. If yes, the process may return to step 334, if no, the process may proceed to step 338. In step 338, back-up battery 106 may be trickle charged from main battery 16.

In step 332, it may be queried whether main battery 16 is in docking station 32. If no, the process may proceed to step 330 where display 59 displays a two-minute countdown. From step 330, the process may proceed to step 331 to execute a complete shutdown of the workstation. If, at step 332, the main battery is in docking station 32, the process may proceed ahead to step 340 to measure the capacity of the main battery, such as by receiving inputs via data interface 160. From step 340, the process may proceed ahead to step 342 to display via display 59 remaining time for the main battery. From step 342, the process may proceed to step 344 to query whether twenty minutes or less remains. If no, the process may return to step 328. If yes, the process may proceed to step 346 wherein display 59 displays a replace battery alert. From step 346, the process may proceed to step 348 to query whether there are zero minutes left. If zero minutes are not left, the process may return to step 346. If, at step 348, zero minutes are left, the process may proceed to step 350 to execute a complete shut down of the workstation. From step 350, the process may proceed to step 352 to finish.

Figure 4:
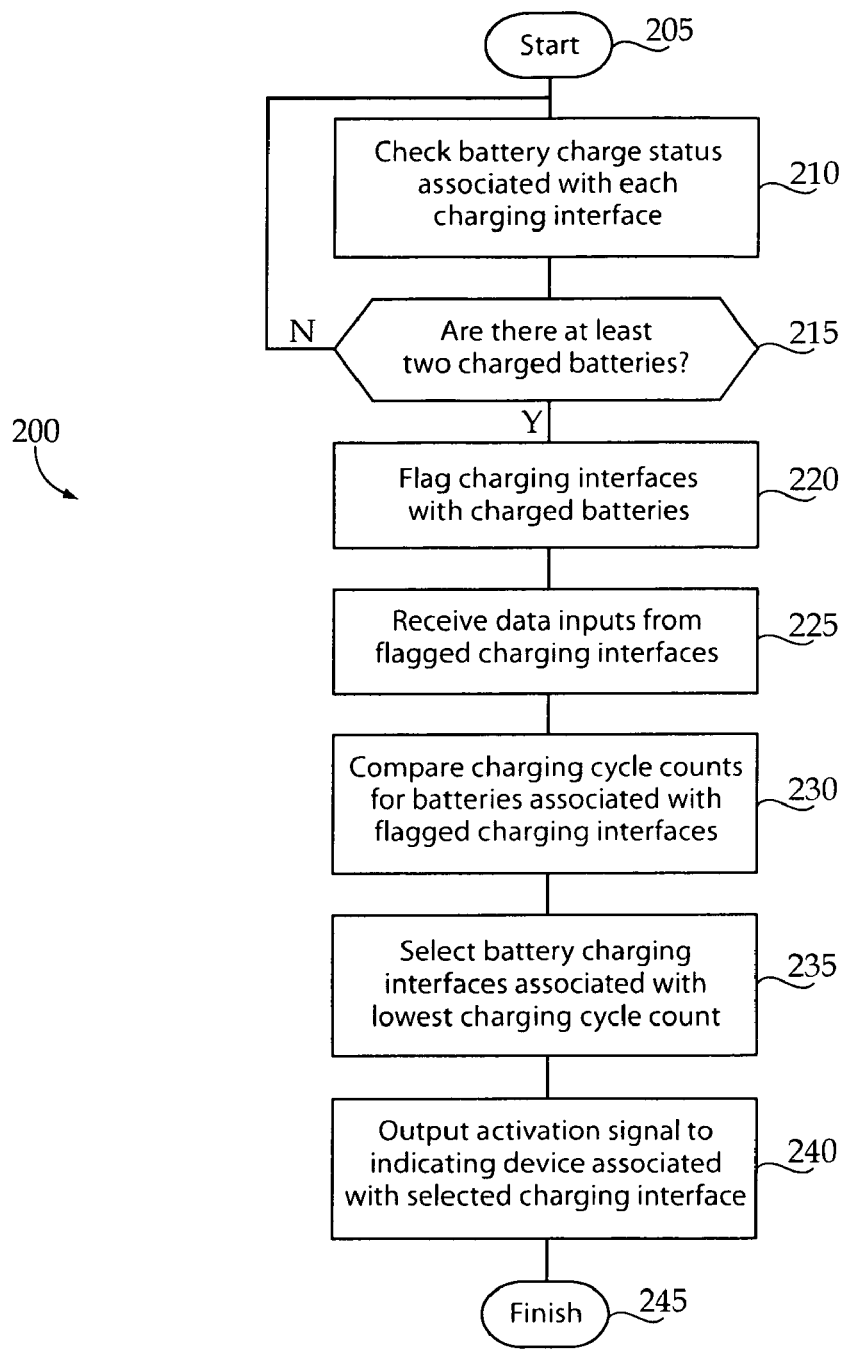
FIG. 4 is a flowchart illustrating an exemplary control process with a battery charger, according to one embodiment.

Referring to FIG. 4, there is shown a flow chart 200 illustrating certain steps in an exemplary control process executed via battery charger 15, and in particular executed via microprocessor 58 of electronic control unit 56. The process of flow chart 200 may begin at a start, step 205, and may then proceed to step 210 wherein microprocessor 58 may check battery charge status associated with each battery charging interface 19. From step 210, the process may proceed to step 215 wherein microprocessor 58 may query whether there are at least two charged batteries simultaneously docked with battery charger 15. If no, the process may return to execute step 210 again or might simply exit. If yes, the process may proceed to step 220 to flag those of battery charging interfaces 19 which have a fully charged battery docked therewith.

From step 220, the process may proceed to step 225 where microprocessor 58 receives data inputs via the flagged battery charging interfaces 19 in indicative of at least one of, battery identification and charging cycle count, for example via communication bus 52. From step 225, the process may proceed to step 230 where microprocessor 58 will compare charging cycle counts for batteries associated with the flagged charging interfaces. From step 230, the process may proceed to step 235 where microprocessor 58 will select a battery charging interface 19 associated with a lowest charging cycle count. From step 235, the process may proceed to step 240 where microprocessor 58 will output an activation signal to one of indicating devices 20 which is associated with the selected charging interface. From step 240, the process may proceed to step 245 to finish.

Figure 16:
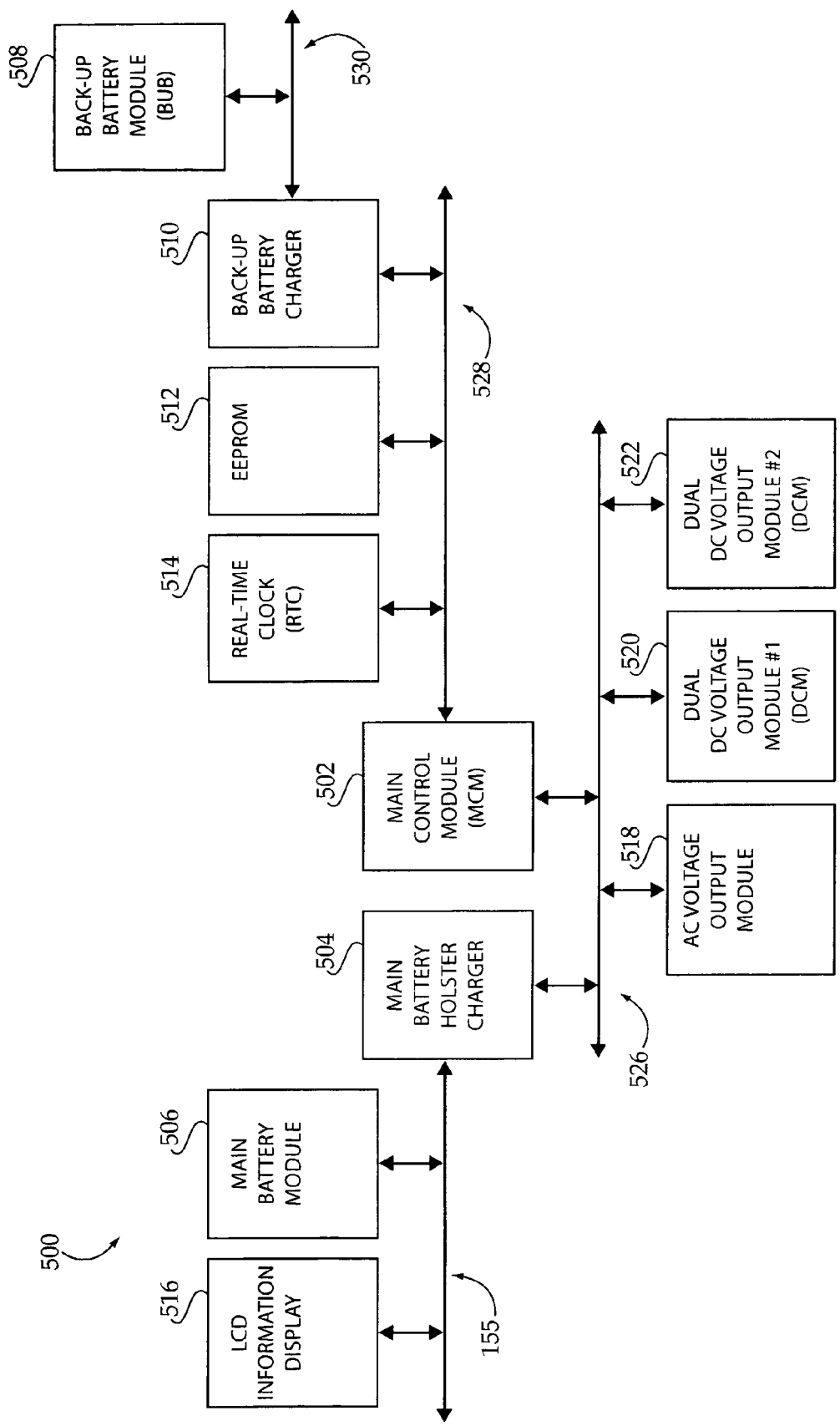
FIG. 16 is a communications block diagram according to one embodiment.

Turning now to FIG. 16, there is shown a communications block diagram representing communication organization and structure in a power system according to the present disclosure such as power system 28. In diagram 500, block 502 is a main control module block, whereas block 504 is a main battery holster charger block. Block 506 is a main battery module block, whereas block 516 is an LCD information display block, each of blocks 506 and 516 communicating with block 504 via a common communication link 155, corresponding with communication link 155 shown in FIG. 13. Block 514 indicates a real time clock, block 512 represents EEPROM or another form of memory and block 510 represents a back-up battery charger. Each of blocks 510, 512 and 514 communicates with block 502 via a common communication link 528. Block 508 represents a back-up battery module, which communicates with block 510. Block 518 represents an AC voltage output module, block 520 represents a dual DC voltage output module and block 522 also represents a dual DC voltage output module. Each of blocks 518, 520 and 522 may be understood as representing a hardware layer, corresponding to devices powered via power system 28, 128 as described herein, and communicating via a common communication link 526 with each of blocks 502 and 504, whereas all of the other blocks may be understood as representing a firmware layer.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. While much of the foregoing description focuses on applications in the mobile workstation arts, the present disclosure is not thereby limited. For example, it is contemplated that battery charging system 14 and the associated strategies for reducing charging cycle count may be broadly applicable outside the mobile workstation context. Embodiments are contemplated where batteries for a system of battery operated devices such as power tools are recharged in accordance with the present disclosure, such as by indicating which of a set of batteries for the system of battery operated devices should be selected to reduce variation in charging cycle count among the batteries of the set. Other aspects, features and advantages will be apparent upon an examination of the attached drawings and appended claims.

We claim:

1. A system for use in gathering or processing data in a healthcare facility comprising:
    a fleet of mobile workstations located in the healthcare facility, and each including a computerized device having a computer readable data storage medium and a battery input interface;
    a set of interchangeable batteries each configured to couple with the battery input interface of any one of the mobile workstations for providing power to the corresponding computerized device; and
    a battery recharging system for the set of interchangeable batteries including a common battery charger having a plurality of docking stations, each of the docking stations including a battery charging interface, and a control device coupled with each of the battery charging interfaces;
    the control device being configured to receive inputs indicative of at least one of, battery identification and charging cycle count, for a plurality of the interchangeable batteries each docked with one of the docking stations, via each of the battery charging interfaces, and to responsively output a battery selection signal, such that the docked interchangeable battery having the lowest charging cycle count is selected for removing from the common battery charger.

2. The system of claim 1 further comprising at least one battery charging cycle counter.

3. The system of claim 2 further comprising a microprocessor resident on the common battery charger, and including the control device.

4. The system of claim 3 wherein the at least one battery charging cycle counter includes a plurality of battery charging cycle counters, each of the battery charging cycle counters being resident on one of the batteries.

5. The system of claim 3 wherein a number of the interchangeable batteries in the set of interchangeable batteries is greater than a number of the mobile workstations in the fleet of mobile workstations.

6. The system of claim 5 further comprising an indicating device resident on the common battery charger, the indicating device having a plurality of different states and being configured to switch between the plurality of different states in response to the battery selection signal.

7. The system of claim 6 wherein the indicating device comprises a plurality of lamps each associated with one of the battery charging interfaces, wherein the microprocessor is configured to illuminate a selected one of the lamps via the battery selection signal.

8. The system of claim 1 wherein each of the mobile workstations of the fleet of mobile workstations includes a power system electrically connected with the corresponding battery input interface, and wherein each of the power systems further includes a back-up battery configured to supply power to the corresponding computerized device when the battery input interface is not coupled with one of the interchangeable batteries of the set.

9. A method of reducing variation in charging cycle count among a plurality of interchangeable batteries for a fleet of mobile workstations comprising the steps of:
    docking a plurality of interchangeable batteries with a common battery charger;
    receiving inputs associated with a charging cycle count for each of the plurality of interchangeable batteries; and
    outputting a battery selection signal which is based at least in part on the inputs, such that the docked battery having the lowest charging cycle count is selected for removing from the common battery charger;
    decoupling a battery from one of the mobile workstations of the fleet of mobile workstations; and
    docking the selected battery with the one of the mobile workstations in place of the decoupled battery.

10. The method of claim 9, further comprising a step of counting charging cycles for each of the plurality of interchangeable batteries.

11. The method of claim 10 wherein the step of counting charging cycles comprises counting charging cycles via a plurality of charging cycle counters each of which is resident on one of the plurality of interchangeable batteries.

12. The method of claim 10 further comprising a step of comparing charging cycle counts for the plurality of interchangeable batteries, and wherein the step of outputting a battery selection signal comprises outputting the battery selection signal in response to comparing charging cycle counts.

13. The method of claim 12 further comprising a step of determining a charge state of each one of the plurality of interchangeable batteries, and wherein the step of outputting a battery selection signal further comprises outputting a battery selection signal based also in part on the determined charge state of each one of the plurality of interchangeable batteries.

14. The method of claim 13 further comprising a step of operating an indicating device of the common battery charger in response to the battery selection signal.

15. The method of claim 14 wherein the step of outputting a battery selection signal further comprises outputting a battery selection signal via a microprocessor resident on the common battery charger.

16. The method of claim 15 further comprising a step of powering a computerized device of the one of the mobile workstations from a back-up battery prior to docking step.

17. A system for use in gathering or processing data in a healthcare comprising:
- a fleet of mobile workstations located in the healthcare facility and each including a computerized device having a computer readable data storage medium, and a battery input interface;
- a set of interchangeable batteries each configured to couple with the battery input interface of any one of the mobile workstations for providing power to the corresponding computerized device;
- a battery recharging system for the set of interchangeable batteries including a common battery charger having a plurality of docking stations and being located at a fixed location within the healthcare facility, such that a use cycle including gathering or processing data with each of the mobile workstations at a plurality of other locations within the healthcare facility begins and ends at the common battery charger; and
- a control device configured to receive data indicative of a charging cycle count of each of the interchangeable batteries when docked with one of the docking stations and responsively output a battery selection signal, such that a first docked interchangeable battery having a lower charging cycle count than a second docked interchangeable battery is selected for removing the common battery charger.

18. The system of claim 17 further comprising an indicating device having a plurality of different states and being configured to switch between the plurality of different states in response to the battery selection signal to indicate the selected interchangeable battery to a user.

19. The system of claim 17 wherein a number of the batteries in the set of interchangeable batteries is greater than a number of the docking stations of the common battery charger and greater than a number of the mobile workstations.

* * * * *